US011138746B2

(12) United States Patent
Kinoshita et al.

(10) Patent No.: US 11,138,746 B2
(45) Date of Patent: Oct. 5, 2021

(54) DIAGNOSTIC SUPPORT SYSTEM AND DIAGNOSTIC SUPPORT METHOD

(71) Applicants: Akira Kinoshita, Kanagawa (JP); Shigenori Kawabata, Tokyo (JP); Masahiro Takada, Tokyo (JP); Kazuya Niyagawa, Kanagawa (JP)

(72) Inventors: Akira Kinoshita, Kanagawa (JP); Shigenori Kawabata, Tokyo (JP); Masahiro Takada, Tokyo (JP); Kazuya Niyagawa, Kanagawa (JP)

(73) Assignees: Ricoh Company, Ltd., Tokyo (JP); NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 335 days.

(21) Appl. No.: 16/007,020

(22) Filed: Jun. 13, 2018

(65) Prior Publication Data

US 2019/0005660 A1   Jan. 3, 2019

(30) Foreign Application Priority Data

Jul. 3, 2017   (JP) .............................. JP2017-130706
Nov. 30, 2017   (JP) .............................. JP2017-230719

(51) Int. Cl.
 *G06T 7/33* (2017.01)
 *A61B 5/00* (2006.01)
 (Continued)

(52) U.S. Cl.
 CPC .............. *G06T 7/337* (2017.01); *A61B 5/242* (2021.01); *A61B 5/407* (2013.01); *A61B 5/4566* (2013.01);
 (Continued)

(58) Field of Classification Search
 CPC . G06T 7/337; G06T 7/74; G06T 2207/30012; G06T 2207/10088; G06T 2207/20221; G16H 30/20; G16H 30/40
 (Continued)

(56) References Cited

U.S. PATENT DOCUMENTS 6,522,908 B1   2/2003   Miyashita et al.
8,559,686 B2   10/2013   Azemoto et al.
(Continued)

FOREIGN PATENT DOCUMENTS

JP   2001-321349   11/2001
JP   2006-288714   10/2006
(Continued)

OTHER PUBLICATIONS

Guan, SY., Wang, TM., Meng, C. et al. A Review of Point Feature Based Medical Image Registration. Chin. J. Mech. Eng. 31, 76 (2018). https://doi.org/10.1186/s10033-018-0275-9 (Year: 2018).*
(Continued)

*Primary Examiner* — Amandeep Saini
(74) *Attorney, Agent, or Firm* — IPUSA, PLLC

(57) ABSTRACT

A diagnostic support system includes a spinal cord/spinal nerve evoked magnetic field data acquisition device configured to acquire spinal cord/spinal nerve evoked magnetic field data and a medical image information acquisition device configured to acquire first medical image information having each pixel associated with a corresponding pixel of visualized data of the spinal cord/spinal nerve evoked magnetic field data. The diagnostic support system superimposes the visualized data of the spinal cord/spinal nerve evoked magnetic field data on second medical image information based on information included in the first medical image information.

3 Claims, 26 Drawing Sheets

(51) Int. Cl.
*A61B 6/00* (2006.01)
*G16H 30/20* (2018.01)
*G16H 30/40* (2018.01)
*G06T 7/73* (2017.01)
*A61B 5/242* (2021.01)
*A61B 5/055* (2006.01)

(52) U.S. Cl.
CPC ............. *A61B 6/505* (2013.01); *A61B 6/506* (2013.01); *A61B 6/5247* (2013.01); *G06T 7/74* (2017.01); *G16H 30/20* (2018.01); *G16H 30/40* (2018.01); *A61B 5/004* (2013.01); *A61B 5/0035* (2013.01); *A61B 5/055* (2013.01); *A61B 5/7425* (2013.01); *G06T 2207/10088* (2013.01); *G06T 2207/20221* (2013.01); *G06T 2207/30012* (2013.01)

(58) Field of Classification Search
USPC .......................................................... 382/131
See application file for complete search history.

(56) References Cited

U.S. PATENT DOCUMENTS

| | | | |
|---|---|---|---|
| 8,620,055 | B2 | 12/2013 | Barratt et al. |
| 8,676,298 | B2 | 3/2014 | Wang et al. |
| 9,135,706 | B2 | 9/2015 | Zagorchev et al. |
| 2007/0121778 | A1 | 5/2007 | Shen et al. |
| 2009/0018431 | A1 | 1/2009 | Feiweier et al. |
| 2015/0173698 | A1 | 6/2015 | Sakaguchi et al. |
| 2015/0190107 | A1* | 7/2015 | Kim ............. A61B 6/032 600/410 |
| 2016/0063697 | A1 | 3/2016 | Yokota et al. |
| 2017/0206670 | A1* | 7/2017 | Miyasa ............. G06K 9/4604 |
| 2018/0092561 | A1 | 4/2018 | Kawabata et al. |
| 2018/0140215 | A1 | 5/2018 | Kawabata |

FOREIGN PATENT DOCUMENTS

| | | |
|---|---|---|
| JP | 4533587 | 9/2010 |
| JP | 2012-045313 | 3/2012 |
| JP | 2013-223620 | 10/2013 |
| JP | 6404277 | 1/2014 |
| JP | 5520378 | 6/2014 |
| JP | 6587614 | 9/2014 |
| JP | 6906015 | 4/2016 |
| JP | 2017-015620 | 1/2017 |
| JP | 2017-051600 | 3/2017 |
| WO | 2009/081297 | 7/2009 |
| WO | 2016/175020 | 11/2016 |
| WO | 2017/043024 | 3/2017 |
| WO | 2017/094221 | 6/2017 |
| WO | 2018/101263 | 6/2018 |

OTHER PUBLICATIONS

Extended European Search Report for 18179558.4 dated Mar. 7, 2019.
Sato T et al : "Functional Imaging of Spinal Cord Electrical Activity From Its Evoked Magnetic Field", IEEE Transactions on Biomedical Engineering, IEEE Service Center, Piscataway, NJ, USA, vol. 56, No. 10, Oct. 11, 2009 (Oct. 1, 2009), pp. 2452-2460, XP011295766, ISSN: 0018-9294 *figures 7,8*.
Yoshiaki Adachi et al : "Recent advancements in the SQUID magnetospinogram system", Superconductor Science and Technology, IOP Publishing, Techno House, Bristol, GB, vol. 30, No. 6, May 3, 2017 (May 3, 2017), p. 63001, XP020316624, ISSN: 0953-2048, DOI : 10.1088/1361-6668/AA66B3 [retrieved on. May 3, 2017] *paragraph [03.2]; figures 2,12,13,14 *.
Satoshi Sumiya et al : "Magnetospinography visualizes electrophysiological activity in the cervical spinal cord", Scientific Reports, vol. 7, No. 1, May 19, 2017 (May 19, 2017), p. 2192, XP055449754, DOI : 10.1038/s41598-017-02406-8 *Results ; figure 2a*.
Tomazevic et al : "3-D / 2-D registration of CT and MR to X-ray images", IEEE Transactions on Medical. Imaging, IEEE Service Center, Piscataway, NJ, US, vol. 22, No. 11, Nov. 1, 2003 (Nov. 11, 2003), pp. 1407-1416, XP011103106, ISSN: 0278-0062, DOI : 10.1109/TM1.2003.819277 *Discussion and Conclusion; p. 1413, left-hand column*.
Rainer Korber et al: "SQUIDs in biomagnetism: a roadmap towards improved healthcare", Superconductor Science and Technology, IOP Publishing, Techno House, Bristol, GB, vol. 29, No. 11, Sep. 19, 2016 (Sep. 19, 2016), p. 113001, XP020309989, ISSN: 0953-2048, DOI: 10.1088/0953-2048/29/11/113001 [retrieved on Sep. 19, 2016] *pp. 3,8; figure 11*.
Japanese Office Action for 2017-230719 dated Aug. 3, 2021.

* cited by examiner

FIG.6A

MEASUREMENT DATA TABLE
(COORDINATE-ADDED X-RAY IMAGE DATA) — 610

| SUBJECT ID | IMAGING DATE/TIME | SUBJECT ATTRIBUTE INFORMATION | IMAGING REGION | DATA ID |
|---|---|---|---|---|
| P101 | 2016/6/10 | AAA | $C_1 \sim C_7$ | X001 |
| | | | | |
| | | | | |

FIG.6B

MEASUREMENT DATA TABLE (RECONSTRUCTION DATA) 620

| SUBJECT ID | IMAGING DATE/TIME | SUBJECT ATTRIBUTE INFORMATION | IMAGING REGION | DATA ID | DATA ID OF CORRESPONDING COORDINATE-ADDED X-RAY IMAGE DATA |
|---|---|---|---|---|---|
| P101 | 2016/6/10 | AAA | $C_1 \sim C_7$ | M001 | X001 |
| | | | | | |
| | | | | | |

FIG.6C

MEASUREMENT DATA TABLE (MRI IMAGE DATA) 630

| SUBJECT ID | IMAGING DATE/TIME | SUBJECT ATTRIBUTE INFORMATION | IMAGING REGION | DATA ID |
|---|---|---|---|---|
| P101 | 2016/6/10 | AAA | $C_1 \sim C_7$ | MR001 |

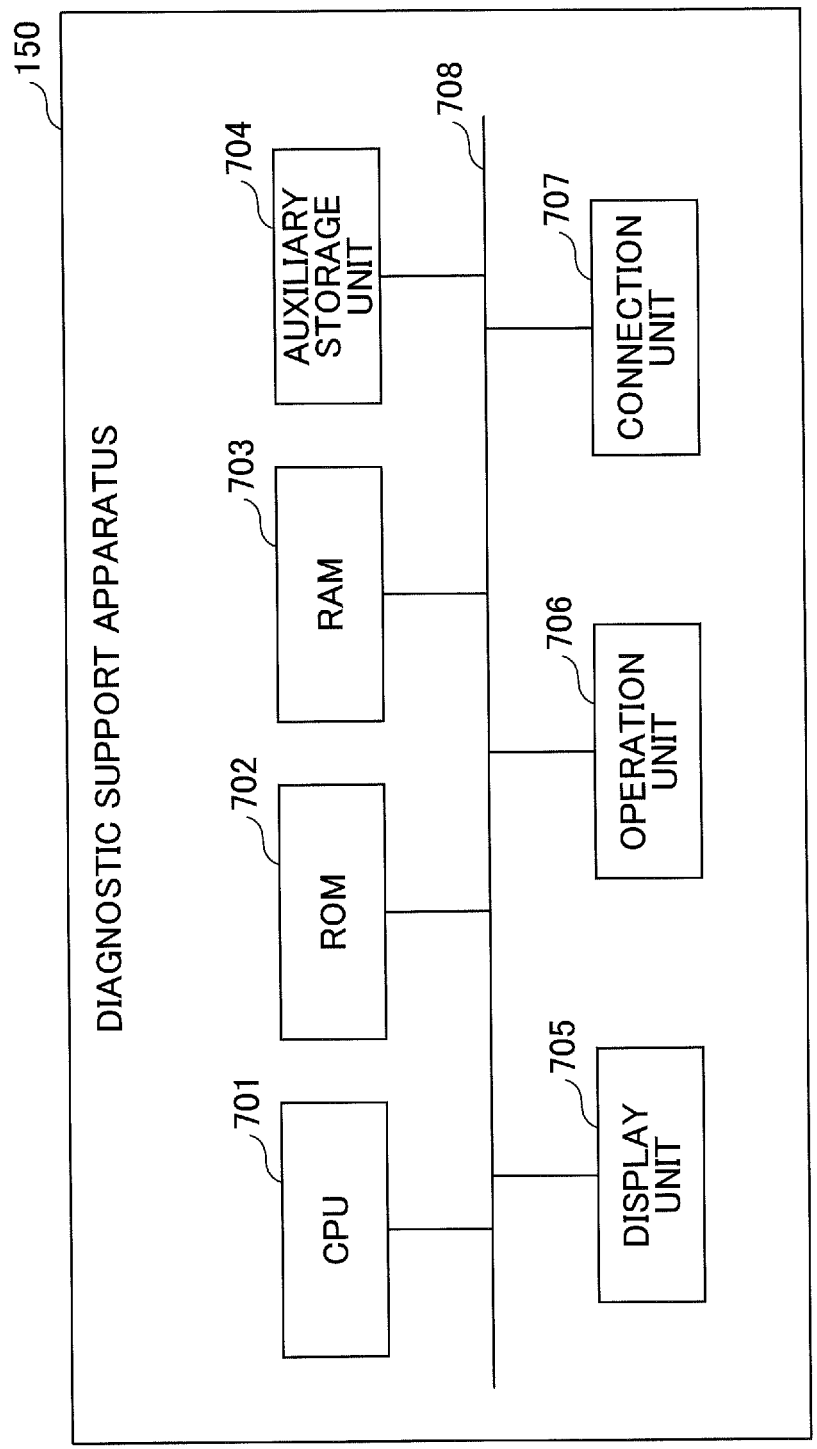

FIG.9

| REGISTRATION DATA LIST | | |
|---|---|---|
| FIRST DATA ID | SECOND DATA ID | TRANSFORM DATA |
| X001 | MR001 | $f(z, y, \theta)$ |
| | | |
| | | |

900

DIAGNOSTIC SUPPORT SYSTEM AND DIAGNOSTIC SUPPORT METHOD

CROSS-REFERENCE TO RELATED APPLICATIONS

The present application claims priority under 35 U.S.C. § 119 to Japanese Patent Application No. 2017-130706 filed on Jul. 3, 2017 and Japanese Patent Application No. 2017-230719 filed on Nov. 30, 2017, the entire contents of which are incorporated herein by reference.

BACKGROUND OF THE INVENTION

1. Field of the Invention

The present invention relates to a diagnostic support system and a diagnostic support method.

2. Description of the Related Art

It is conventional medical practice to obtain multiple medical images by imaging or measuring the same region of a subject and generating image data based on the imaging results or measurement results so that the multiple medical images may be used for diagnosing the region or designing a treatment plan, for example. In the case of using multiple medical images as described above, diagnostic accuracy may be improved and treatment planning may be simplified by superimposing medical images of a target organ or region (e.g., diagnosis target organ or region) and displaying the superimposed image, for example.

In this respect, for example, International Publication WO 2009/081297 describes an image processing technique that involves extracting a set of features corresponding to a combination of features from each of a plurality of medical images and performing image registration using the extracted sets of features.

However, in the case of using medical images, it may not always be possible to generate images of a diagnosis target organ or region. Also, depending on the imaging method or the measuring method used, it may be difficult to determine the position of the diagnosis target organ or region, for example. In such cases, it may be difficult to properly superimpose and display multiple medical images even when using the image processing technique described above.

SUMMARY OF THE INVENTION

One aspect of the present invention is directed to providing a technique for properly superimposing and displaying multiple medical images of a target organ or region.

A diagnostic support system includes a spinal cord/spinal nerve evoked magnetic field data acquisition device configured to acquire spinal cord/spinal nerve evoked magnetic field data and a medical image information acquisition device configured to acquire first medical image information having each pixel associated with a corresponding pixel of visualized data of the spinal cord/spinal nerve evoked magnetic field data. The diagnostic support system superimposes the visualized data of the spinal cord/spinal nerve evoked magnetic field data on second medical image information based on information included in the first medical image information.

BRIEF DESCRIPTION OF THE DRAWINGS

FIGS. 6A-6C are diagrams illustrating example measurement data tables stored in a measurement data storage unit;

FIG. 7 is a diagram illustrating an example hardware configuration of a diagnostic support apparatus;

FIG. 9 is a diagram illustrating an example registration data list;

DESCRIPTION OF THE EMBODIMENTS

Figure 1:
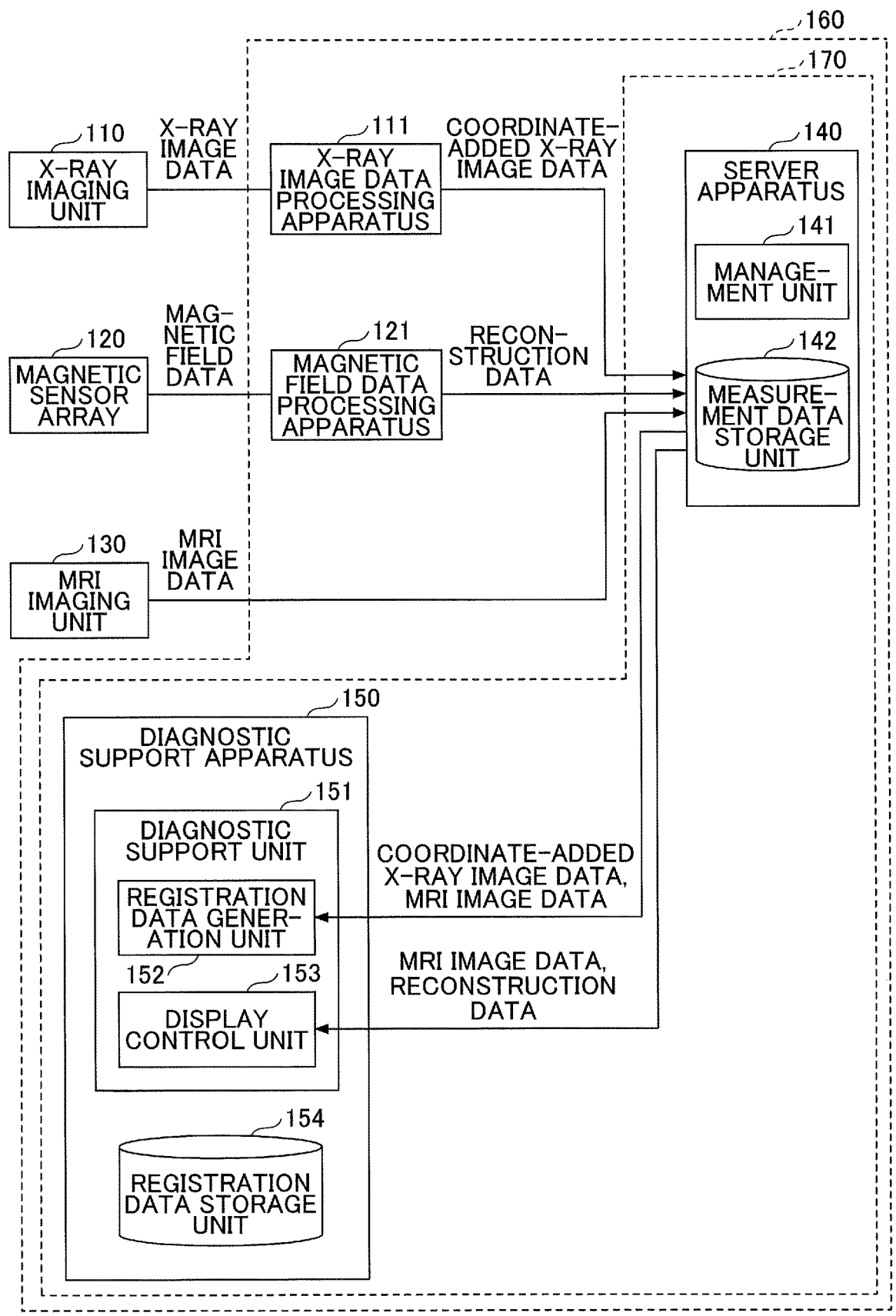
FIG. 1 is a diagram illustrating an example overall configuration of a diagnostic support system.

In the following, overall features of diagnostic support systems according to embodiments of the present invention will be described. The diagnostic support systems according to the embodiments described below generate registration data for superimposing a plurality of medical images of a target organ or region (e.g., diagnosis target organ or region; "spinal cord" in the embodiments described below). Specifically, the diagnostic support systems generate registration data for superimposing a plurality of medical images including: reconstruction data obtained by reconstructing magnetic field data measured by a magnetic array sensor (i.e., estimating/re-calculating current sources within the body based on the magnetic field data and visualizing the magnetic field data); and MRI (magnetic resonance imaging) image data captured by a MRI imaging unit.

In the case of using reconstruction data, the diagnosis target organ or region of a subject cannot be imaged, and as such, the position of the diagnosis target organ or region cannot be directly ascertained from the reconstruction data. Thus, in the diagnostic support systems according to the embodiments described below, first, when measuring the magnetic field data using the magnetic array sensor, an X-ray imaging unit is used to capture X-ray image data, and pixels of the X-ray image data and pixels of the reconstruction data are associated with each other. Then, registration data for superimposing the X-ray image data on the MRI image data is generated, and the generated registration data is used in superimposing the reconstruction data on the MRI image data. That is, the diagnostic support systems according to the embodiments described below generate registration data for superimposing X-ray image data and MRI image data as a plurality of medical images.

Note that the X-ray image data and the MRI image data are obtained using different imaging methods, and not all relevant organs/regions may be imaged in the X-ray image data and the MRI image data. Thus, the diagnostic support systems according to the embodiments described below are configured to estimate the position of an organ/region that could not be imaged based on an organ/region that could be imaged so that the diagnosis target organ/region in the X-ray image data can be superimposed on the target organ/region in the MRI image data.

Note that in the following embodiments, example cases of generating registration data for superimposing X-ray image data on MRI image data Will be primarily described. However, the medical images to be superimposed are not limited to X-ray image data and MRI image data and may be a combination of medical images other than the combination of X-ray image data and MRI image data. Also, the number of medical images to be superimposed and displayed may be three or more, for example. Further, the plurality of medical images to be used for generating registration data is not limited to medical images that are obtained using different imaging methods or different measuring methods. That is, medical images obtained by the same imaging method or the same measuring method may be used as well.

In the following, embodiments of the present invention will be described with reference to the accompanying drawings. In the following description and the drawings, elements having substantially the same functional configuration are given the same reference numerals and overlapping descriptions may be omitted.

First Embodiment

<1. Diagnostic Support System Overall Configuration>

First, the overall configuration of a diagnostic support system according to an embodiment of the present invention will be described. FIG. 1 is a diagram showing an example overall configuration of a diagnostic support system 100.

In FIG. 1, the diagnostic support system 100 includes an X-ray imaging unit 110, an X-ray image data processing apparatus 111, a magnetic sensor array 120, a magnetic field data processing apparatus 121, and an MRI imaging unit 130. Further, the diagnostic support system 100 includes a server apparatus 140 and a diagnostic support apparatus 150.

The X-ray imaging unit 110 emits X-rays on a subject and detects X-rays that have passed through the subject to generate X-ray image data of the subject. The X-ray imaging unit 110 transmits the generated X-ray image data to the X-ray image data processing apparatus 111.

Based on the X-ray image data received from the X-ray imaging unit 110, the X-ray image data processing apparatus 111 generates a coordinate axis with respect to a predetermined position of the magnetic sensor array 120 and generates coordinate-added X-ray image data (described below). Further, the X-ray image data processing apparatus 111 transmits the generated coordinate-added X-ray image data to the server apparatus 140.

The magnetic sensor array 120 is a biosensor having a plurality of magnetic sensors arranged in an array. The magnetic sensor array 120 applies a predetermined electric stimulus to a subject to measure the current flowing through a nerve in the spinal cord of the subject as magnetic field data. The magnetic field data measured by each of the plurality of magnetic sensors included in the magnetic sensor array 120 is input to the magnetic field data processing apparatus 121.

By processing the magnetic field data received from the magnetic sensor array 120, the magnetic field data processing apparatus 121 calculates reconstruction data indicating the currents flowing through points in the spinal cord of the subject (visualized data obtained by estimating current sources within the body based on spinal cord/spinal nerve evoked magnetic field data). The magnetic field data processing apparatus 121 transmits the calculated reconstruction data to the server apparatus 140.

The MRI imaging unit 130 uses radio waves to activate the fluid within the body of a subject to capture a tomographic image of the subject and generate MRI image data. The MRI imaging unit 130 transmits the generated MRI image data to the server apparatus 140.

The server apparatus 140 is an information processing apparatus that manages various data. A management program is installed in the server apparatus 140. The server apparatus 140 executes the management program to implement functions of a management unit 141.

The management unit 141 receives the coordinate-added X-ray image data transmitted from the X-ray image data processing apparatus 111, the reconstruction data transmitted from the magnetic field data processing apparatus 121, and the MRI image data transmitted from the MRI imaging unit 130. Also, the management unit 141 stores the received data as measurement data in a measurement data storage unit 142.

Also, in response to a request from the diagnostic support apparatus 150, the management unit 141 retrieves the measurement data stored in the measurement data storage unit 142 and transmits the measurement data to the diagnostic support apparatus 150.

The diagnostic support apparatus 150 is an information processing apparatus that assists a doctor or some other health professional (simply referred to as "doctor" hereinafter) in diagnosing nerve activity of a subject. A diagnostic support program is installed in the diagnostic support apparatus 150. The diagnostic support apparatus 150 executes the diagnostic support program to implement functions of a diagnostic support unit 151.

The diagnostic support unit 151 includes a registration data generation unit 152 as an example of a generation unit and a display control unit 153 as an example of a control unit.

The registration data generation unit 152 retrieves from the server apparatus 140, the coordinate-added X-ray image data and the MRI image data stored as measurement data of the subject in the measurement data storage unit 142. Also, the registration data generation unit 152 of the diagnostic support unit 151 generates registration data for superimposing the coordinate-added X-ray image data on the MRI image data, and stores the generated registration data in a registration data storage unit 154.

The display control unit 153 retrieves from the server apparatus 140, the MRI image data and the reconstruction data stored as measurement data of the subject in the measurement data storage unit 142. Also, the display control unit 153 refers to the registration data storage unit 154 to retrieve corresponding registration data, transforms coordinates of the reconstruction data using the corresponding registration data, superimposes the transformed reconstruction data on the MRI image data, and displays the superimposed reconstruction data and MRI image data.

Note that in the example system configuration of FIG. 1 as described above, the diagnostic support system 100 includes the X-ray imaging unit 110, the magnetic sensor array 120, and the MRI imaging unit 130. However, a diagnostic support system according to an embodiment of the present invention does not necessarily have to include such measurement devices. For example, the coordinate-added X-ray image data may be generated using X-ray image data that is stored in advance in the X-ray image data processing apparatus 111. Also, the reconstruction data may be generated using magnetic field data that is stored in advance in the magnetic field data processing apparatus 121, for example. That is, a diagnostic support system according to another embodiment may only include the elements within the range defined by dotted line 160 of FIG. 1, for example.

Further, a diagnostic support system according to an embodiment of the present invention does not necessarily have to include the X-ray image data processing apparatus 111 and the magnetic field data processing apparatus 121. For example, the diagnostic support unit 151 may be configured to use measurement data that are already stored in the server apparatus 140. That is, a diagnostic support system according to another embodiment may only include the elements within the range defined by dotted line 170, for example.

<2. Medical Service Operation Flow>

Figure 2:
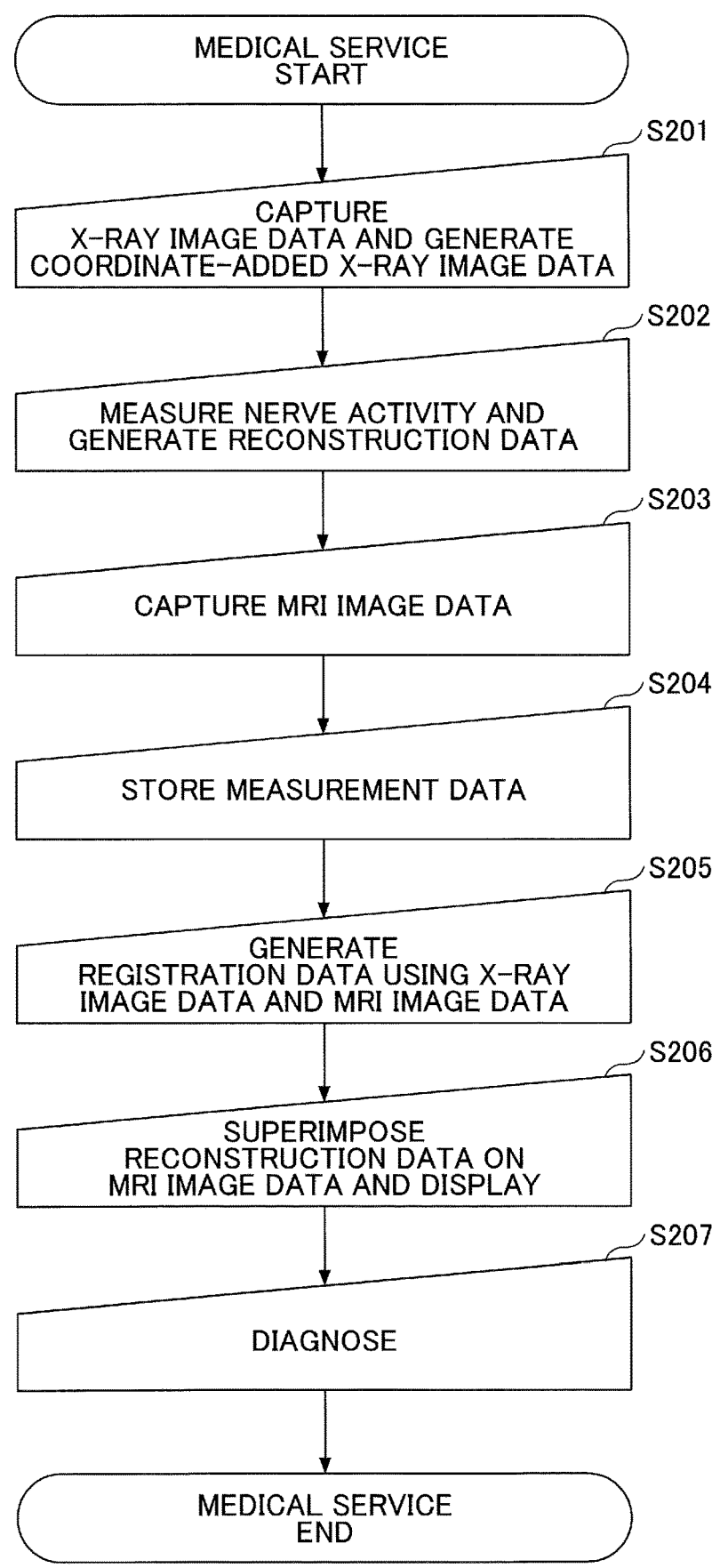
FIG. 2 is a flowchart illustrating medical service operations performed using the diagnostic support system.

In the following, an overall flow of medical service operations performed using the diagnostic support system 100 will be described. FIG. 2 is a flowchart illustrating example medical service operations performed using the diagnostic support system 100.

In step S201, a doctor uses the diagnostic support system 100 to capture X-ray image data of a subject and generate coordinate-added X-ray image data. In this way, a position of an organ/region of the subject in the coordinate-added X-ray image data can be calculated based on the position of the coordinate axis with respect to the predetermined position of the magnetic sensor array 120.

In step S202, the doctor uses the diagnostic support system 100 to measure data for diagnosing nerve activity of the subject. Specifically, the doctor applies electrical stimulation to the subject and uses the magnetic sensor array 120 to measure the current flowing through a nerve within the spinal cord of the subject as magnetic field data. In this way, reconstruction data is generated.

In step S203, the doctor uses the diagnostic support system 100 to capture MRI image data.

In step S204, the doctor uses the diagnostic support system 100 to store measurement data (coordinate-added X-ray image data, reconstruction data, and MRI image data) in the measurement data storage unit 142.

In step S205, the doctor uses the diagnostic support system 100 to retrieve the X-ray image data and the MRI image data stored in the measurement data storage unit 142 and generate registration data.

In step S206, the doctor uses the diagnostic support system 100 to retrieve the reconstruction data and the MRI image data stored in the measurement data storage unit 142, transform coordinates of the reconstruction data using the generated registration data, superimpose the transformed reconstruction data on the MRI image data, and display the superimposed reconstruction data and MRI image data.

In step S207, the doctor diagnoses the neural activity of the subject based on the superimposed reconstruction data and MRI image data that is displayed.

In the following, functions and operations of the diagnostic support system 100 associated with steps S201 to S206 of the above process steps of FIG. 2 (steps S201 to S207) will be described.

<3. Step S201: Capturing X-ray Image Data and Generating Coordinate-Added X-Ray Image Data>

First, functions and operations of the diagnostic support system 100 associated with step S201 (capturing X-ray image data and generating coordinate-added X-ray image data) will be described.

<3.1 Method of Capturing X-Ray Image Data>

Figure 3:
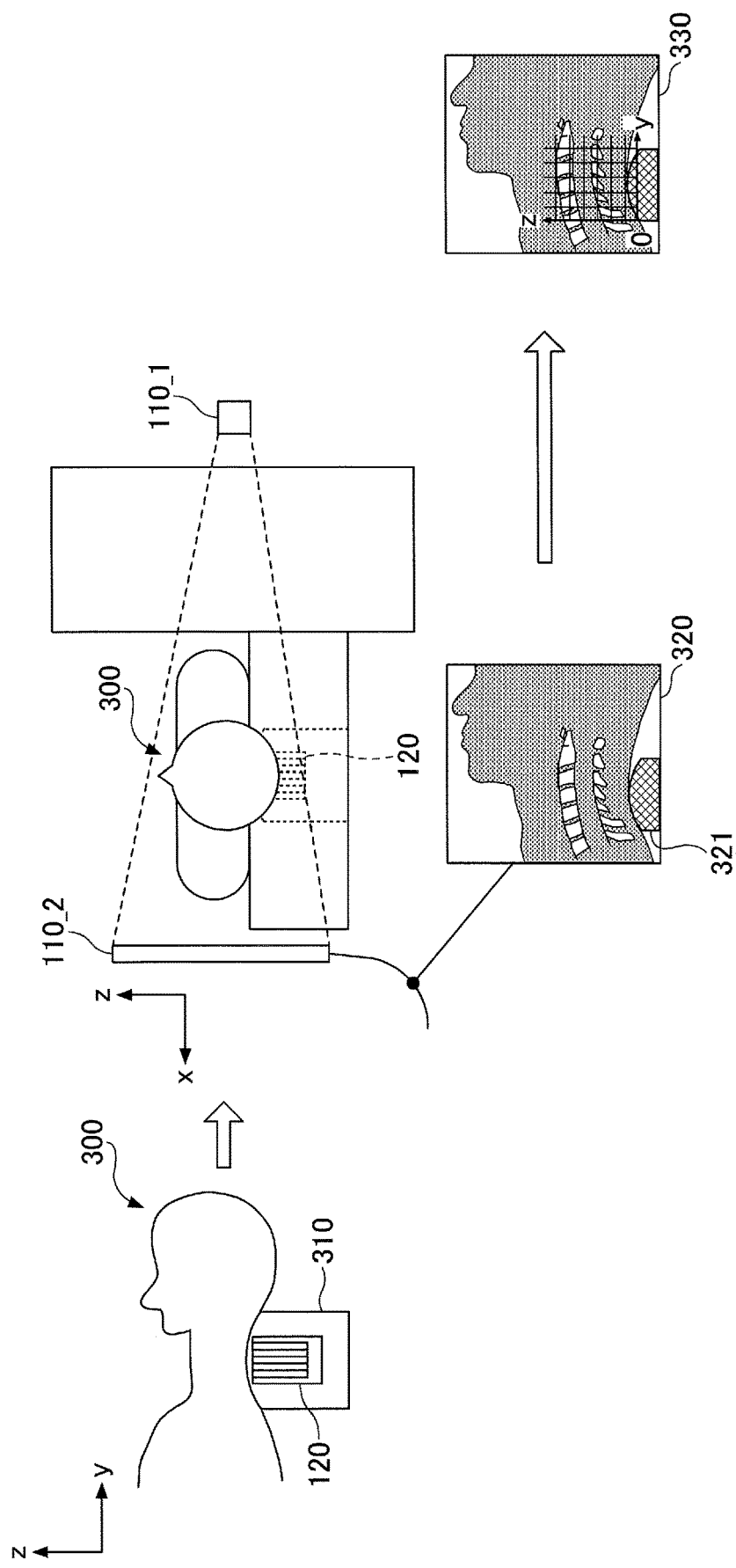
FIG. 3 is a diagram illustrating an imaging method for capturing X-ray image data and a method of generating coordinate-added X-ray image data.

FIG. 3 is a diagram illustrating a method of capturing X-ray image data and a method of generating coordinate-added X-ray image data according to the present embodiment. As can be appreciated from FIG. 3, in the present embodiment, xyz coordinates are defined as follows.

x-axis: axis extending from the right arm to the left arm of subject 300.

y-axis: axis extending from the chest to the head of the subject 300.

z-axis: axis extending from the back to the chest of the subject 300.

The X-ray image data of the subject 300 is captured while the subject 300 is in the same posture as that when the magnetic field of the subject 300 is measured using the magnetic sensor array 120. The magnetic sensor array 120 is arranged inside a dewar 310, and the magnetic sensor array 120 measures the magnetic field while the subject 300 is lying on his/her back so that the upper surface of the dewar 310 comes into contact with a region around the spine of the subject 300. The X-ray image data of the subject 300 is captured while the subject 300 is in the same posture as described above.

FIG. 3 illustrates how the subject 300 is imaged from a lateral side using the X-ray imaging unit 110. The X-ray imaging unit 110 includes an X-ray source 110_1 and an X-ray detector 110_2. The X-ray imaging unit 110 irradiates X-rays from a lateral side of the subject 300 to capture an X-ray image of the subject 300 and output X-ray image data 320.

By capturing the X-ray image data using the X-ray imaging unit 110 while the subject 300 is in the same posture as that when the magnetic field is measured using the magnetic sensor array 120, an image element 321 of the magnetic sensor array 120 may be included in the X-ray image data 320 captured by the X-ray imaging unit 110.

<3.2 Method of Generating Coordinate-Added X-Ray Image Data>

In the following, a method of generating coordinate-added X-ray image data will be described. Upon receiving the X-ray image data 320 from the X-ray imaging unit 110, the X-ray image data processing apparatus 111 detects the image element 321 of the magnetic sensor array 120 included in the X-ray image data 320. Also, the X-ray image data processing apparatus 111 calculates the yz coordinates of each pixel in the X-ray image data 320 with respect to a predetermined position of the image element 321 of the magnetic sensor array 120 detected in the X-ray image data 320 as the origin. In this way, the X-ray image data processing apparatus 111 generates coordinate-added X-ray image data 330. That is, the coordinate-added X-ray image data 330 generated by the X-ray image data processing apparatus 111 corresponds image data that assigns xy coordinates with respect to a predetermined position of the magnetic sensor array 120 (origin) to each pixel of the X-ray image data 320.

Note that although grid lines representing the yz coordinates are indicated on the coordinate-added X-ray image data 330 in FIG. 3 for convenience of illustration, such grid lines may not be displayed when the coordinate-added X-ray image data 330 is actually presented to a doctor.

<4. Step S202: Measuring Nerve Activity and Generating Reconstruction Data>

In the following, functions and operations of the diagnostic support system 100 associated with step S202 (measuring nerve activity and generating reconstruction data) will be described.

<4.1 Method of Measuring Magnetic Field>

Figure 4:
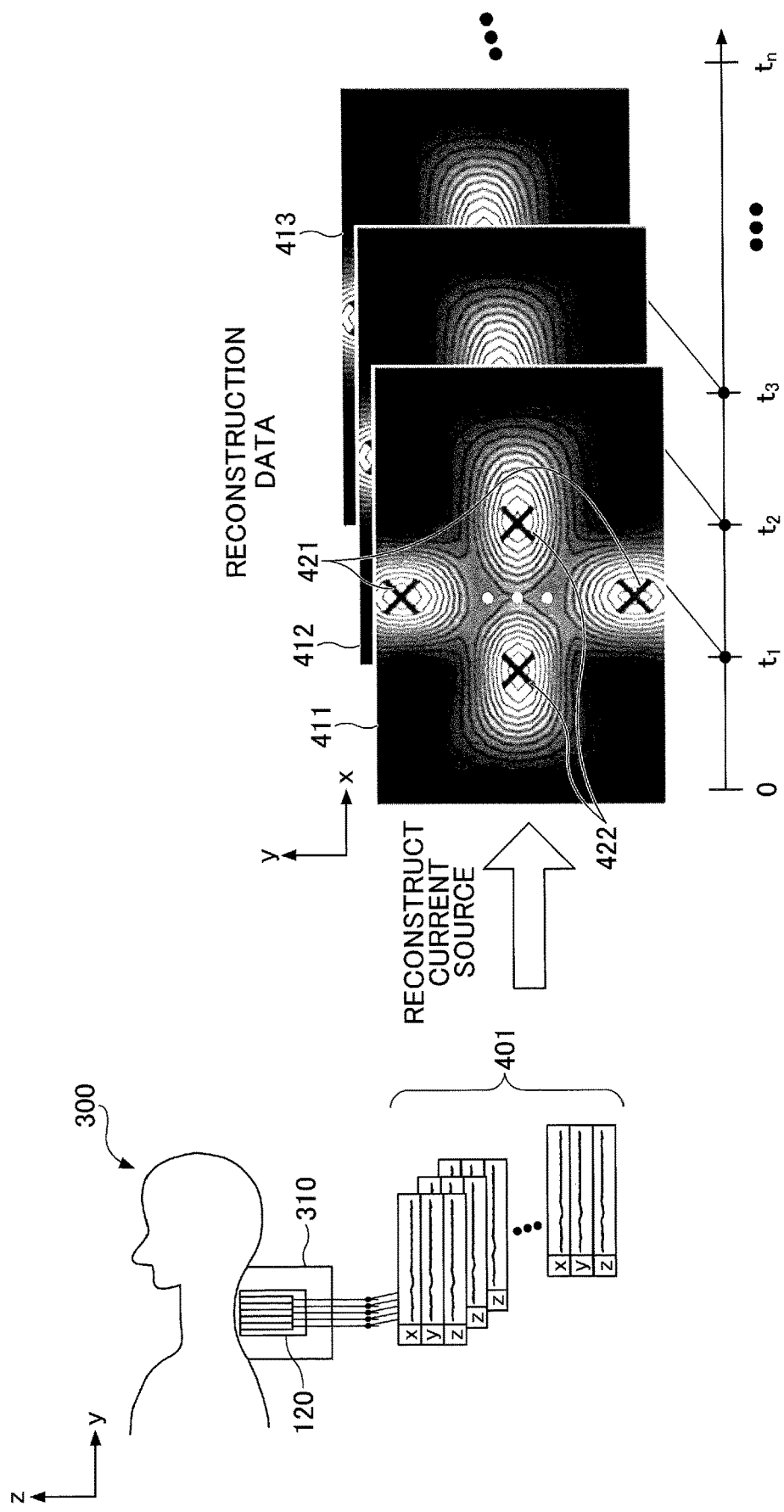
FIG. 4 is a diagram illustrating a magnetic field measuring method for acquiring magnetic field data and a method of generating reconstruction data.

FIG. 4 is a diagram showing a method of measuring magnetic field data and a method of generating reconstruction data. As illustrated in FIG. 4, the upper surface of the dewar 310 is in contact with a dorsal-side region around the spine of the subject 300 that is lying on his/her back. In such a state, an electrode is attached to a predetermined arm portion (e.g., a left arm portion) of the subject 300 and an electric stimulus is applied to the subject 300 so that the magnetic sensor array 120 can measure the current flowing through the nerves in the spinal cord of the subject 300 as magnetic fields.

Each of the magnetic sensors constituting the magnetic sensor array 120 measures the magnetic field in each of the x-axis, the y-axis, and the z-axis for a predetermined time. In the present embodiment, voltage signals that have been obtained by the magnetic sensors measuring the magnetic fields in the above axes for a predetermined time are referred to as magnetic field data 401.

<4.2 Method of Generating Reconstruction Data>

As illustrated in FIG. 4, each magnetic sensor of the magnetic sensor array 120 outputs three voltage signals. Further, the magnetic sensor array 120 as a whole outputs the magnetic field data 401, which is made up of voltage signals amounting to three times the total number of magnetic sensors included in the magnetic sensor array 120.

For example, assuming that the number of magnetic sensors included in the magnetic sensor array 120 is 35 (5×7 array), at least 105 voltage signals are output as the magnetic field data 401 from the magnetic sensor array 120. Note that each voltage signal includes voltage signals measured during a period from the time an electrical stimulation is applied to the subject 300 (e.g., time 0) until time $t_n$.

FIG. 4 illustrates how the magnetic field data processing apparatus 121 generates reconstruction data by reconstructing current sources (estimates and visualizes the current sources) using the magnetic field data 401 output by the magnetic sensor array 120. Frames 411 to 413 of the reconstruction data illustrated in FIG. 4 are generated by estimating and visualizing the current sources in a predetermined xy plane ($z=z_0$) at times $t_1$, $t_2$, and $t_3$.

In each of the frames 411 to 413 of the reconstruction data, white portions represent current values with a large absolute value, and black portions represent current values with a small absolute value. Further, in each of the frames 411 to 413 of the reconstruction data, cross marks 421 represent the positions of peak values of the intracellular current, and cross marks 422 represent the positions of peak values of the volume current. As the time advances, the positions of the cross marks 421 and 422 move in the y-axis direction.

The frame 411 of the reconstruction data at time $t_1$ is calculated based on the magnetic field data 401 at time $t_1$ (the voltage signals in the x-axis, the y-axis, and the z-axis output by each magnetic sensor). Note that although FIG. 4 illustrates frames on the xy plane where $z=z_0$ as an example, the magnetic field data processing apparatus 121 can calculate frames on xy planes at different positions in the z-axis direction.

Similarly, the frame 412 of the reconstruction data at time $t_2$ is calculated based on the magnetic field data 401 at time $t_2$ (the voltage signals in the x-axis, the y-axis, and the z-axis output by each magnetic sensor). Although FIG. 4 illustrates frames on the xy plane where $z=z_0$ as an example, the magnetic field data processing apparatus 121 can calculate frames on xy planes at different positions in the z-axis direction.

Similarly, the frame 413 of the reconstruction data at the time $t_3$ is calculated based on the magnetic field data 401 at time $t_3$ (the voltage signals in the x-axis, the y-axis, and the z-axis output by each magnetic sensor). Although FIG. 4 illustrates frames on the xy plane where $z=z_0$ as an example, the magnetic field data processing apparatus 121 can calculate frames on xy planes at different positions in the z-axis direction.

Note that in each of the frames 411 to 413 of the reconstruction data, the predetermined position of the magnetic sensor array 120 (the position corresponding to the origin of the coordinate system defining the coordinates of the coordinate-added X-ray image data 330) is known. Also, positions within each of the frames 411 to 413 of the reconstruction data are defined by coordinates of a coordinate system with an origin at the predetermined position of the magnetic sensor array 120.

In other words, coordinates assigned to the coordinate-added X-ray image data 330 and coordinates assigned to the frames 411 to 413 of the reconstruction data are all based on the predetermined position of the magnetic sensor array 120 as the origin. Thus, coordinates of the coordinate-added X-ray image data 330 and coordinates of the frames 411 to 413 of the reconstruction data that are identical refer to the same position of the subject 300.

By correlating the pixels of the frames 411 to 413 of the reconstruction data with the pixels of the coordinate-added X-ray image data 330 as described above, each position within each of the frames 411 to 413 can be correlated with a corresponding position of the subject 300 based on the coordinate-added X-ray image data 330. For example, by assigning coordinates of an organ/region of the subject 300 included in the coordinate-added X-ray image data 330 to a corresponding position in each of the frames 411 to 413 of the reconstruction data, a position in each of the frames 411 to 413 can be correlated with a corresponding position of the organ/region of the subject 300.

<5. Step S203: Capturing MRI Image Data>

Figure 5:
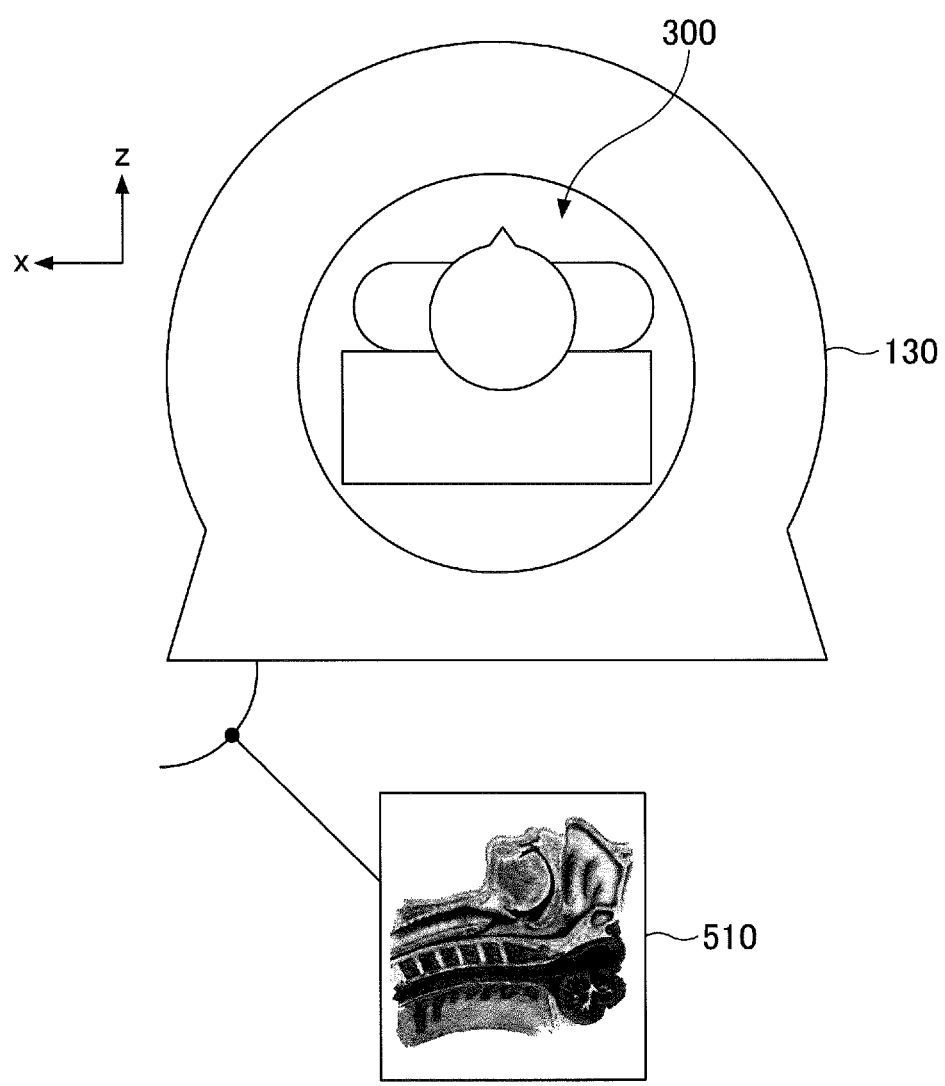
FIG. 5 is a diagram illustrating an imaging method for capturing MRI image data.

In the following, functions and operations of the diagnostic support system 100 associated with step S203 (capturing MRI image data) will be described. FIG. 5 is a diagram illustrating a method of capturing MRI image data. In FIG. 5, the MRI imaging unit 130 captures MRI image data of the subject 300. The MRI image data is also captured with the subject 300 lying on his/her back. However, because an apparatus including the MRI imaging unit 130 that is used to capture MRI image data is different from the apparatus including the X-ray imaging unit 110 and the magnetic sensor array 120, the MRI image data is captured at a different time from when the X-ray image data and the magnetic field data are obtained. The MRI imaging unit 130 images the subject 300 and outputs MRI image data 510 of the subject 300.

<6. Step S204: Storing Measurement Data>

In the following, functions and operations of the diagnostic support system associated with step S204 (storing measurement data) will be described. FIGS. 6A-6C are diagrams illustrating example measurement data tables stored in the measurement data storage unit 142. FIG. 6A is a diagram illustrating a measurement data table (coordinate-added X-ray image data) 610 that stores coordinate-added X-ray image data. In FIG. 6A, the measurement data table (coordinate-added X-ray image data) 610 includes fields for storing information items "subject ID", "imaging date/time", "subject attribute information", "imaging region", and "data ID".

The "subject ID" is for storing an identifier identifying the subject 300. The "imaging date/time" stores the date and time the X-ray image data was captured. The "subject attribute information" stores attribute information, such as the name, age, sex, height, and weight, of the subject 300. Note that the attribute information stored in the "subject attribute information" is input by a doctor when capturing the X-ray image data of the subject 300.

The "imaging region" is for storing the region of the subject 300 imaged by the X-ray imaging unit 110. The "data ID" is for storing an identifier identifying the coordinate-added X-ray image data of the subject 300.

FIG. 6B is a diagram illustrating a measurement data table (reconstruction data) 620 that stores reconstruction data. In FIG. 6B, the measurement data table (reconstruction data) 620 includes fields for storing information items similar to those included in the measurement data table (coordinate-added X-ray image data) 610. However, the measurement data table (reconstruction data) 620, additionally includes a field for storing information item "data ID of corresponding coordinate-added X-ray image data". The "data ID of corresponding coordinate-added X-ray image data" is for storing the data ID of the coordinate-added X-ray image data captured and generated upon measuring the magnetic field data used for generating the reconstruction data.

FIG. 6C is a diagram illustrating a measurement data table (MRI image data) 630 that stores MRI image data. In FIG. 6C, the measurement data table (MRI image data) 630 includes fields for storing information items similar to those included in the measurement data table (coordinate-added X-ray image data) 610.

<7. Step S205: Registration; and Step S206: Superimposition and Display>

In the following, functions and operations of the diagnostic support system 100 associated with step S205 (registration) and step S206 (superimposition and display) will be described.

<7.1 Hardware Configuration of Diagnostic Support Apparatus>

First, the hardware configuration of the diagnostic support apparatus 150 associated with step S205 (registration) and step S206 (superimposition and display) will be described. FIG. 7 is a diagram illustrating an example hardware configuration of the diagnostic support apparatus 150.

In FIG. 7, the diagnostic support apparatus 150 includes a CPU (Central Processing Unit) 701, a ROM (Read Only Memory) 702, and a RAM (Random Access Memory) 703. The CPU 701, the ROM 702, and the RAM 703 form a so-called computer. Further, the diagnostic support apparatus 150 includes an auxiliary storage unit 704, a display unit 705, an operation unit 706, and a connection unit 707. The above components of the diagnostic support apparatus 150 are connected to each other via a bus 708.

The CPU 701 is a device that executes various programs (e.g., diagnostic support program) stored in the auxiliary storage unit 704.

The ROM 702 is a nonvolatile main storage device. The ROM 702 stores various programs and data necessary for the CPU 701 to execute various programs stored in the auxiliary storage unit 704. More specifically, the ROM 702 stores a boot program such as BIOS (Basic Input/Output System) or EFI (Extensible Firmware Interface).

The RAM 703 is a volatile main storage device such as a DRAM (Dynamic Random Access Memory) or a SRAM (Static Random Access Memory). The RAM 703 functions as a work area that is used by the CPU 701 when the CPU 701 executes various programs stored in the auxiliary storage unit 704.

The auxiliary storage unit 704 is an auxiliary storage device that stores various programs to be executed by the CPU 701 and various data generated by the CPU 701 executing various programs. The registration data storage unit 154 described above may be implemented by the auxiliary storage unit 704.

The display unit 705 is a display device that superimposes reconstruction data on MRI image data and displays the superimposed reconstruction data and MRI image data. The operation unit 706 is an input device for enabling a doctor to input various instructions (e.g., data selection instruction, superimposition and display instruction) to the diagnostic support apparatus 150. The connection unit 707 is a communication device for communicating with the server apparatus 140.

Steps S205 and S206 may be implemented by the diagnostic support apparatus 150 having the hardware configuration as described above. Note that although not particularly mentioned in the above descriptions of steps S201 to S204, the X-ray image data processing apparatus 111, the magnetic field data processing apparatus 121, and the server apparatus 140 may also have hardware configurations substantially identical to the above-described hardware configuration of the diagnostic support apparatus 150.

<7.2 Registration Data Generation Unit of Diagnostic Support Apparatus>

(1) Functional Configuration of Registration Data Generation Unit

In the following, the functional configuration of the diagnostic support apparatus 150 will be described. As described above, the diagnostic support apparatus 150 implements functions of the diagnostic support unit 151. The diagnostic support unit 151 includes the registration data generation unit 152 and the display control unit 153. The functions of the registration data generation unit 152 of the diagnostic support unit 151 are described in detail below.

Figure 8:
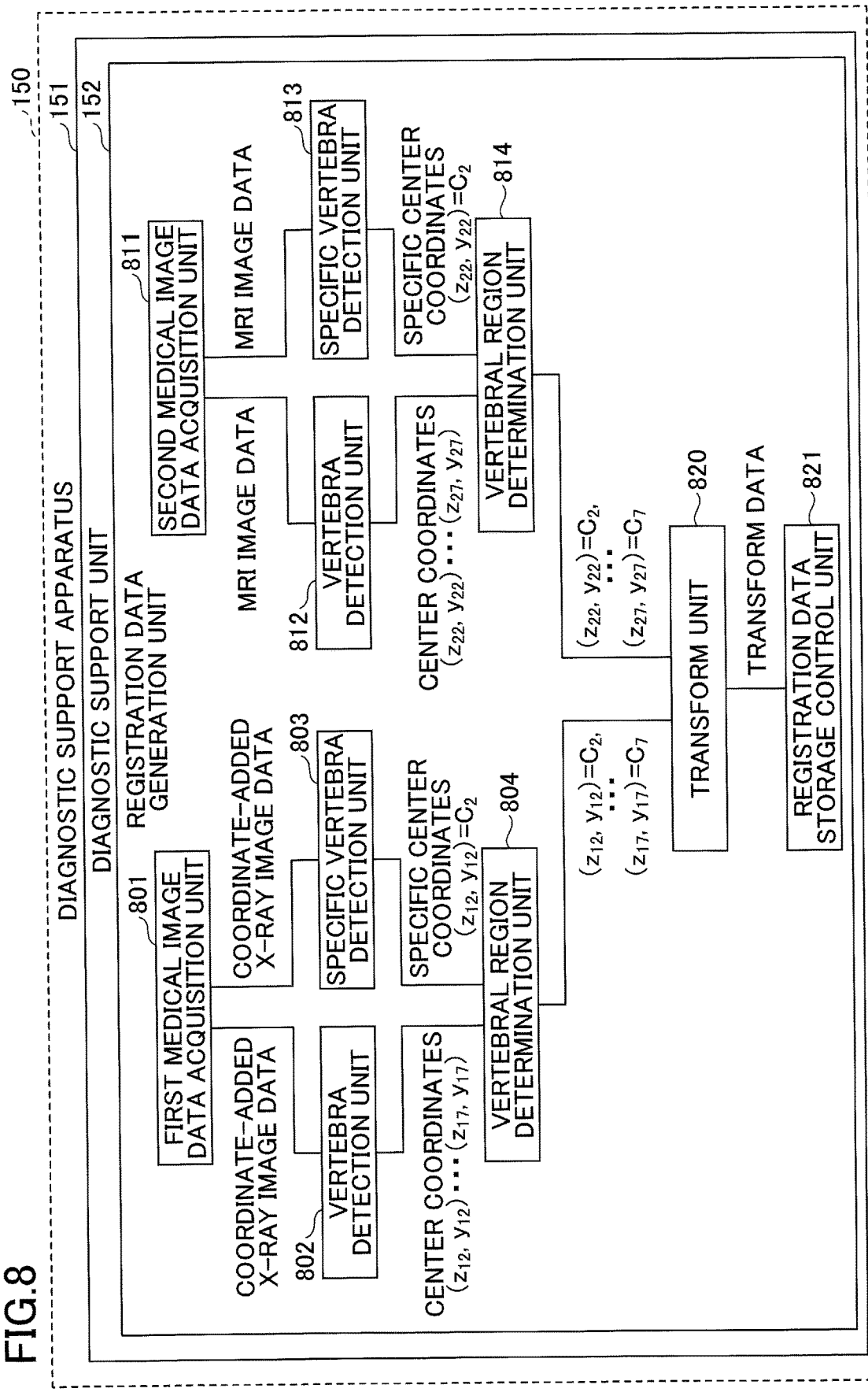
FIG. 8 is a diagram illustrating a first example functional configuration of a registration data generation unit.

FIG. 8 is a diagram illustrating an example functional configuration of the registration data generation unit 152. In FIG. 8, the registration data generation unit 152 includes a first medical image data acquisition unit 801, a vertebra detection unit 802, a specific vertebra detection unit 803, and a vertebral region determination unit 804. Further, the registration data generation unit 152 includes a second medical image data acquisition unit 811, a vertebra detection unit 812, a specific vertebra detection unit 813, and a vertebra region determination unit 814. Further, the registration data generation unit 152 includes a transform unit 820 and a registration data storage control unit 821.

The first medical image data acquisition unit 801 retrieves the coordinate-added X-ray image data stored in the measurement data storage unit 142 of the server apparatus 140 as first medical image data (also referred to as "first medical image information"). The coordinate-added X-ray image data retrieved by the first medical image data acquisition unit 801 is selected by a doctor, for example. The first medical image data acquisition unit 801 communicates the retrieved coordinate-added X-ray image data to the vertebra detection unit 802 and the specific vertebra detection unit 803.

The vertebra detection unit 802 performs image processing on the coordinate-added X-ray image data communicated from the first medical image data acquisition unit 801 to extract a vertebrae or a vertebral part of the subject 300 from the coordinate-added X ray image data. Specifically, the vertebra detection unit 802 extracts an area smaller than a detection target area of the coordinate-added X-ray image data and determines whether the extracted small area corresponds to a vertebra or a vertebral part.

The vertebra detection unit 802 may extract a small area from the coordinate-added X-ray image data using a sliding window, for example. Alternatively, the vertebra detection unit 802 may extract a small area from the coordinate-added X-ray image data using edge extraction processing or ASM (Active Shape Model), for example. Alternatively, the vertebra detection unit 802 may extract a small area from the coordinate-added X-ray image data using object detection processing, for example.

Also, the vertebra detection unit 802 determines whether the extracted small area corresponds to a vertebra or a vertebral part using an image processing technique such as CNN (Convolutional Neural Network) or SVM (Support Vector Machine), for example.

Upon determining that an extracted small area corresponds to a vertebra or a vertebral part, the vertebra detection unit 802 communicates the center coordinates of the extracted small area to the vertebral region determination unit 804 as position information of the vertebra or the vertebral part. In the present example, it is assumed that six small areas have been determined to correspond to vertebrae or vertebral parts, and the respective center coordinates ($z_{12}$, $y_{12}$), ..., ($Z_{17}$, $y_{17}$) of the six small areas are communicated to the vertebral region determination unit 804.

The specific vertebra detection unit 803 performs image processing on the coordinate-added X-ray image data communicated from the first medical image data acquisition unit 801, extracts a specific vertebra or a specific vertebral part of the subject 300 to be used as a reference. A specific vertebra or a specific vertebral part to be used as a reference corresponds to a vertebra or a vertebral part (referential organ) having morphological information distinct from other vertebrae or vertebral parts. For example, the vertebral body of the second cervical vertebra (C2) may be extracted as a specific vertebral part to be used as a reference.

Specifically, the specific vertebra detection unit 803 extracts an area smaller than a detection target area within the coordinate-added X-ray image data and determines whether the extracted small area corresponds to a specific vertebra or a specific vertebral part to be used as a reference. Note that the methods implemented by the specific vertebra detection unit 803 for extracting the small area and determining whether the extracted small area corresponds to a specific vertebra or a specific vertebral part to be used as a reference may be substantially identical to the above-described small area extraction method and determination method implemented by the vertebra detection unit 802.

Upon determining that a specific small area corresponds to a specific vertebra or a specific vertebral part to be used as a reference, the specific vertebra detection unit 803 communicates the center coordinates (specific center coordinates) of the specific small area to the vertebral region determination unit 804 as position information of the specific vertebra or the specific vertebral part to be used as a reference. In the present example, it is assumed that the vertebral body of the second cervical vertebra (C2) is extracted as the specific vertebral part to be used as a reference, and the specific center coordinates ($z_{12}$, $y_{12}$) of the corresponding small area are communicated to the vertebral region determination unit 804 as the position information of the specific vertebral part to be used as a reference.

The vertebral region determination unit 804 is an example of a first determination unit that determines the correlation between the center coordinates communicated from the vertebra detection unit 802 and corresponding vertebrae or vertebral parts based on the specific center coordinates communicated from the specific vertebra detection unit 803.

Specifically, the vertebral region determination unit 804 compares the center coordinates of the six small areas communicated from the vertebra detection unit 802 with the specific center coordinates of the specific small area communicated from the specific vertebra detection unit 803, and determines the center coordinates of one small area from among the six small areas representing the closest point to the specific center coordinates. The vertebral region determination unit 804 further determines that the center coordinates of the one small area closest to the specific center coordinates corresponds to the center coordinates of the second cervical vertebra (C2) vertebral body.

Further, the vertebral region determination unit 804 determines that the center coordinates of the other five small areas from among the six small areas that are located below the center coordinates of the second cervical vertebra (C2) vertebral body respectively correspond to center coordinates of the third cervical vertebra (C3) vertebral body, center coordinates of the fourth cervical vertebra (C4), center coordinates of the fifth cervical vertebra (C5), center coordinates of the sixth cervical vertebra (C6), and center coordinates of the seventh cervical vertebra (C7) vertebral body.

The vertebral region determination unit 804 determines the correlation between the center coordinates ($z_{12}$, $y_{12}$), ..., ($Z_{17}$, $y_{17}$) and the second cervical vertebra (C2) vertebral body to the seventh cervical vertebra (C7) vertebral body in the manner described above and communicates the determination results to the transform unit 820.

The second medical image data acquisition unit 811 retrieves the MRI image data stored in the measurement data storage unit 142 of the server apparatus 140 as second medical image data (also referred to as "second medical image information"). The MRI image data retrieved by the second medical image data acquisition unit 811 is selected by a doctor, for example. The second medical image data acquisition unit 811 communicates the retrieved MRI image data to the vertebra detection unit 812 and the specific vertebra detection unit 813.

The vertebra detection unit 812 performs image processing on the MRI image data communicated from the second medical image data acquisition unit 811 to extract a vertebrae or a vertebral part of the subject 300 from the MRI image data. Specifically, the vertebra detection unit 812 extracts an area smaller than a detection target area within the MRI image data and determines whether the extracted small area corresponds to a vertebra or a vertebral part.

The vertebra detection unit 812 may extract a small area from the MRI image data using a sliding window, for example. Alternatively, the vertebra detection unit 812 may extract a small area from the MRY image data using edge extraction processing or ASM (Active Shape Model), for example. Alternatively, the vertebra detection unit 812 may extract a small area from the MRI image data using object detection processing, for example.

Also, the vertebra detection unit 812 may determine whether the extracted small area corresponds to a vertebra or a vertebral part using an image processing technique, such as CNN or SVM, for example.

Upon determining that an extracted small area corresponds to a vertebra or a vertebral part, the vertebra detection unit 812 communicates the center coordinates of the extracted small area to the vertebral region determination unit 814 as the position information of the vertebra or the vertebral part. In the present example, it is assumed that six small areas have been determined to correspond to vertebrae or vertebral parts, and the respective center coordinates ($z_{22}$, $y_{22}$), . . . , ($z_{27}$, $y_{27}$) of the six areas are communicated to the vertebral region determination unit 814 as position information of the vertebrae or vertebral parts.

The specific vertebra detection unit 813 performs image processing on the MRI image data communicated from the second medical image data acquisition unit 811 to extract a specific vertebra or a specific vertebral part of the subject 300 to be used as a reference. A specific vertebra or a specific vertebral part to be used as a reference corresponds to a vertebra or a vertebral part (referential organ) having morphological information distinct from other vertebrae or other vertebral parts. For example, the vertebral body of the second cervical vertebra (C2) may be extracted as a specific vertebral part to be used as a reference.

Specifically, the specific vertebra detection unit 813 extracts an area smaller than a detection target area within the MRI image data and determines whether the extracted small area corresponds to a specific vertebra or a specific vertebral part to be used as a reference. Note that the methods implemented by the specific vertebra detection unit 813 for extracting a small area and determining whether the extracted small area corresponds to a specific vertebra or a specific vertebral part to be used as a reference may be substantially identical to the above-described small area extraction method and determination method implemented by the vertebra detection unit 812.

Upon determining that a specific small area corresponds to a specific vertebra or a specific vertebral part to be used as a reference, the specific vertebra detection unit 813 communicates the center coordinates (specific center coordinates) of the specific small area to the vertebral region determination unit 814 as position information of the specific vertebra or the specific vertebral part to be used as a reference. In the present example, it is assumed that the vertebral body of the second cervical vertebra (C2) is extracted as a specific vertebral part to be used as a reference, and the specific center coordinates ($z_{22}$, $y_{22}$) are communicated to the vertebral region determination unit 814 as position information of the specific vertebral part to be used as a reference.

The vertebral region determination unit 814 is an example of a second determination unit that determines the correlation between the center coordinates communicated from the vertebra detection unit 812 and corresponding vertebrae or vertebral parts based on the specific center coordinates communicated from the specific vertebra detection unit 813.

Specifically, the vertebral region determination unit 814 compares the center coordinates of the six small areas communicated from the vertebra detection unit 812 with the specific center coordinates of the specific small area communicated from the specific vertebra detection unit 813, and determines the center coordinates of one small area from among the six small areas representing the closest point to the specific center coordinates. The vertebral region determination unit 814 further determines that the center coordinates of the one small area closest to the specific center coordinates corresponds to center coordinates of the second cervical vertebra (C2) vertebral body.

Further, the vertebral region determination unit 814 determines that the center coordinates of the other five small areas from among the six small areas that are located below the center coordinates of the second cervical vertebra (C2) vertebral body respectively correspond to center coordinates of the third cervical vertebra (C3) vertebral body, center coordinates of the fourth cervical vertebra (C4), center coordinates of the fifth cervical vertebra (C5), center coordinates of the sixth cervical vertebra (C6), and center coordinates of the seventh cervical vertebra (C7) vertebral body.

The vertebral region determination unit 814 determines the correlation between the center coordinates ($z_{22}$, $y_{22}$), . . . , ($z_{27}$, $y_{27}$) and the second cervical vertebra (C2) vertebral body to the seventh cervical vertebra (C7) vertebral body in the manner described above and communicates the determination results to the transform unit 820.

The transform unit 820 computes registration data (transform data) for superimposing the coordinate-added X-ray image data on the MRI image data using the center coordinates communicated from the vertebral region determination unit 804 and the center coordinates communicated from the vertebral region determination unit 814. For example, the transform unit 820 may compute a transform function for transforming and superimposing the coordinate-added X-ray image data on the MRI image data as registration data (transform data). Alternatively, the transform unit 820 may compute corresponding point information (coordinate data associating each set of coordinates (z, y) of the coordinate-added X-ray image data with a corresponding set of coordinates (z, y) of the MRI image data) for superimposing the coordinate-added X-ray image data on the MRI image data as the registration data, for example.

Specifically, the transform unit 820 estimates positions of the spinal cord of the subject 300 in the coordinate-added X-ray image data based on the center coordinates communicated from the vertebral region determination unit 804. Also, the transform unit 820 estimates or extracts positions of the spinal cord of the subject 300 in the MRI image data based on the center coordinates communicated from the vertebral region determination unit 814. Further, the transform unit 820 transforms the coordinates of the pixels of the coordinate-added X-ray image data such that the estimated (or extracted) positions of the spinal cord in the coordinate-added X-ray image data may be superimposed on corresponding positions in the MRI image data. The transform unit 820 communicates the transform data used in the above pixel coordinate transformation to the registration data storage control unit 821 as registration data.

The registration data storage control unit 821 associates the registration data communicated from the transform unit 820 with a data ID identifying the coordinate-added X-ray image data and a data ID identifying the MRI image data, and stores the associated registration data in the registration data storage unit 154.

(2) Registration Data List generated by Registration Data Generation Unit

In the following, a specific example of a registration data list that is generated by the registration data generation unit 152 and stored in the registration data storage unit 154 will be described. FIG. 9 is a diagram illustrating an example registration data list 900.

In FIG. 9, the registration data list 900 includes columns "first data ID", "second data ID", and "transform data" as information items.

The "first data ID" is for storing the data ID of the coordinate-added X-ray image data retrieved by the first medical image data acquisition unit 801. The "second data ID" is for storing the data ID of the MRI image data retrieved by the second medical image data acquisition unit 811. The "transform data" is for storing the transform data communicated from the transform unit 820 as registration data.

(3) Determination Process by Registration Data Generation Unit

In the following, a determination process (process operations from retrieving a medical image to determining regions corresponding to vertebrae) executed by the registration data generation unit 152 is described.

(i) Determination Process Flow

Figure 10:
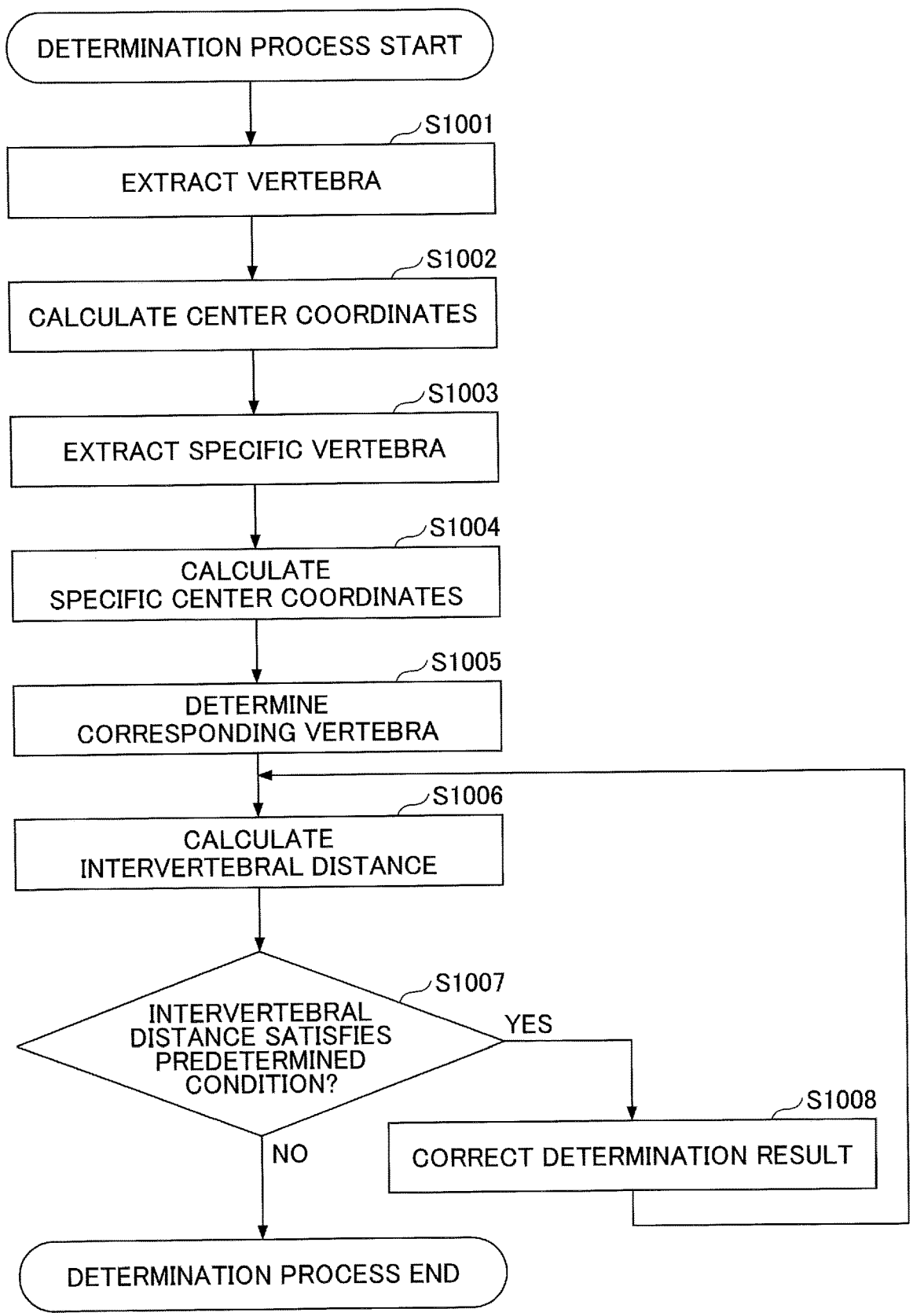
FIG. 10 is a flowchart illustrating a determination process.

FIG. 10 is a flowchart illustrating an example process flow of the determination process executed by the registration data generation unit 152. The determination process of FIG. 10 starts when the first medical image data acquisition unit 801 retrieves coordinate-added X-ray image data and the second medical image data acquisition unit 811 retrieves MRI image data from the server apparatus 140.

In step S1001, the vertebra detection unit 802 extracts a vertebra or a vertebral part from the coordinate-added X-ray image data by extracting a small area from the coordinate-added X-ray image data and determining whether the extracted small area corresponds to a vertebra or a vertebral part. Similarly, the vertebra detection unit 812 extracts a vertebra or a vertebral part from the MRI image data by extracting a small area from the MRI image data and determining whether the extracted small area corresponds to a vertebra or a vertebral part.

In step S1002, the vertebra detection unit 802 calculates the center coordinates of the vertebra or the vertebral part extracted from the coordinate-added X-ray image data. Similarly, the vertebra detection unit 812 calculates the center coordinates of the vertebra or the vertebral part extracted from the MRI image data.

In step S1003, the specific vertebra detection unit 803 extracts the second cervical vertebra (C2) vertebral body from the coordinate-added X-ray image data by extracting a small area from the coordinate-added X-ray image data and determining whether the extracted small area corresponds to the second cervical vertebra (C2) vertebral body. Similarly, the specific vertebra detection unit 813 extracts the second cervical vertebra (C2) vertebral body from the MRI image data by extracting a small area from the MRI image data and determining whether the extracted small area corresponds to the second cervical vertebra (C2) vertebral body.

In step S1004, the specific vertebra detection unit 803 calculates the specific center coordinates of the second cervical vertebra (C2) vertebral body extracted from the coordinate-added X-ray image data. Similarly, the specific vertebra detection unit 813 calculates the specific center coordinates of the second cervical vertebra (C2) vertebral body extracted from the MRI image data.

In step S1005, the vertebral region determination unit 804 determines the correlation between the center coordinates extracted by the vertebra detection unit 802 and corresponding vertebrae or corresponding vertebral parts based on the specific center coordinates of the second cervical vertebra (C2) vertebral body extracted by the specific vertebra detection unit 803. Similarly, the vertebral region determination unit 814 determines the correlation between the center coordinates extracted by the vertebra detection unit 812 and corresponding vertebrae or corresponding vertebral parts based on the specific center coordinates of the second cervical vertebra (C2) vertebral body extracted by the specific vertebra detection unit 813.

In step S1006, the vertebral region determination unit 804 calculates, for each of the vertebrae or vertebral parts, an intervertebral distance between the corresponding vertebra or vertebral part and an adjacent vertebra or vertebral part. Similarly, the vertebral region determination unit 814 calculates, for each of the vertebrae or vertebral parts, an intervertebral distance between the corresponding vertebra or vertebral part and an adjacent vertebra or vertebral part.

In step S1007, the vertebral region determination unit 804 determines whether any one of the calculated intervertebral distances satisfies a predetermined condition, and if the predetermined condition is satisfied, the vertebral region determination unit 804 proceeds to step S1008. Specifically, the vertebral region determination unit 804 determines that the predetermined condition is satisfied and proceeds to step S1008 in the following scenario:

One intervertebral distance from among the calculated intervertebral distances substantially differs from the average value of the calculated intervertebral distances; and The one intervertebral distance is about twice the length of the other intervertebral distances.

Similarly, the vertebral region determination unit 814 determines whether any one of the calculated intervertebral distances satisfies a predetermined condition, and if the predetermined condition is satisfied, the vertebral region determination unit 814 proceeds to S1008. Specifically, the vertebral region determination unit 814 determines that the predetermined condition is satisfied and proceeds to step S1008 in the following scenario:

One intervertebral distance from among the calculated intervertebral distances substantially differs from the average value of the calculated distances; and The one intervertebral distance is about twice the length of the other intervertebral distances.

In step S1008, the vertebral region determination unit 804 corrects the determination results and returns to step S1006. In this way, even when a vertebra or a vertebral part could not be extracted from the coordinate-added X-ray image data, the vertebral region determination unit 804 can make accurate determinations with respect to the extracted vertebrae or vertebral parts.

Similarly, the vertebral region determination unit 814 corrects the determination results and returns to step S1006. In this way, even when a vertebra or a vertebral part could not be extracted from the MRI image data, the vertebral region determination unit 814 can make accurate determinations with respect to the extracted vertebrae or vertebral parts.

On the other hand, if the vertebral region determination unit 804 and the vertebral region determination unit 814 determine in step S1007 that none of the calculated intervertebral distances satisfies the predetermined condition, the determination process is ended.

(ii) Determination Process for Coordinate-Added X-Ray Image Data

Figure 11:
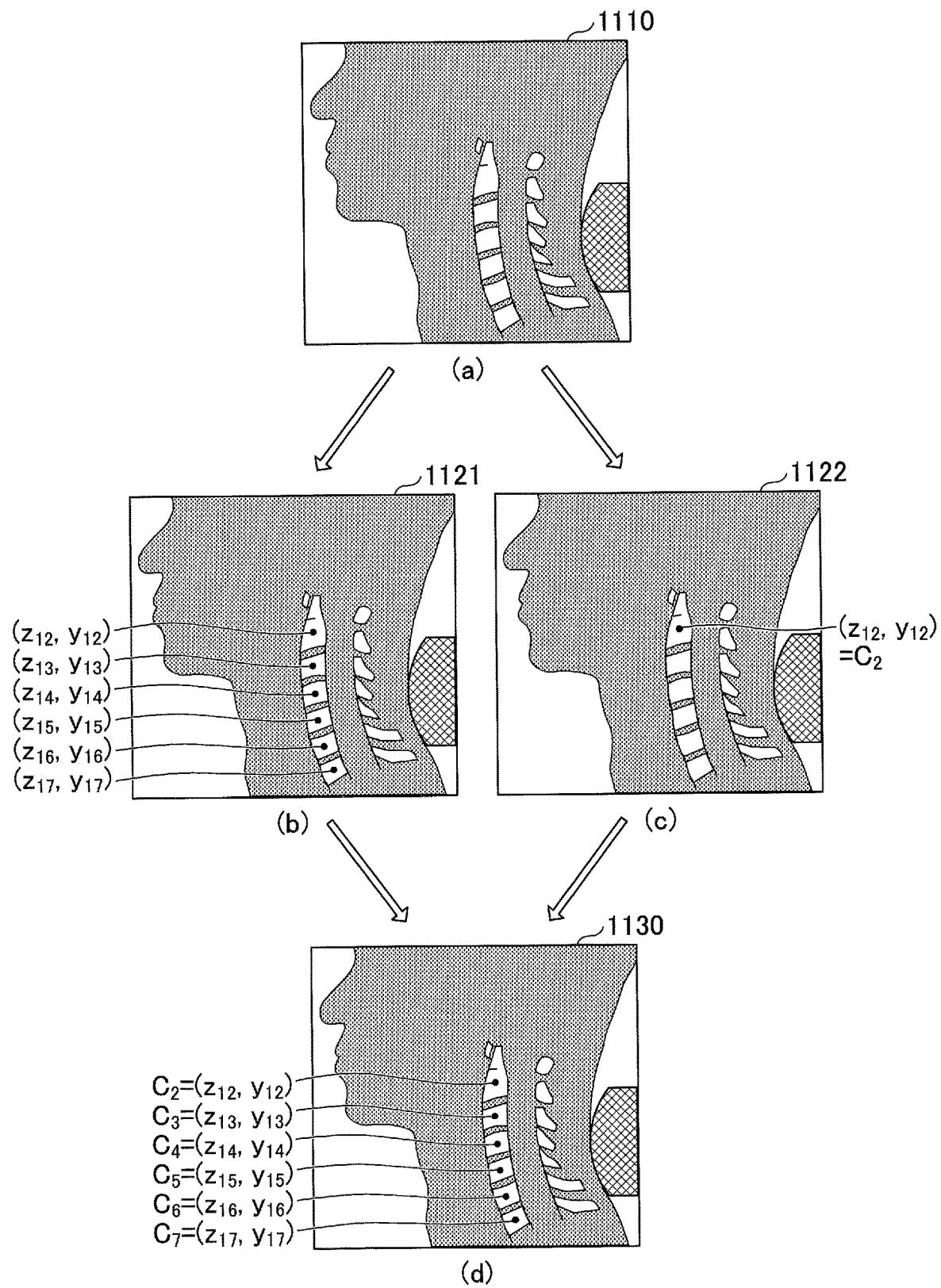
FIG. 11 is a diagram illustrating a first specific example of the determination process executed with respect to coordinate-added X-ray image data.

In the following, a specific example of the determination process executed with respect to coordinate-added X-ray image data will be described. FIG. 11 is a diagram illustrating a first specific example of the determination process executed with respect to coordinate-added X-ray image data. In FIG. 11, coordinate-added X-ray image data 1110 represents an example of the coordinate-added X-ray image data retrieved by the first medical image data acquisition unit 801.

In FIG. 11, coordinate-added X-ray image data 1121 represents an example of the coordinate-added X-ray image data obtained as a result of the vertebra detection unit 802 performing image processing on the coordinate-added X-ray image data 1110 to extract vertebrae or vertebral parts of the of the subject 300 and calculate the center coordinates of the extracted vertebrae or vertebral parts.

In FIG. 11, coordinate-added X-ray image data 1122 represents an example of coordinate-added X-ray image data obtained as a result of the specific vertebra detection unit 803 performing image processing on the coordinate-added X-ray image data 1110 to extracts the second cervical vertebra (C2) vertebral body of the subject 300 and calculate the specific center coordinates of the second cervical vertebra (C2) vertebral body.

In FIG. 11, coordinate-added X-ray image data 1130 represents an example of coordinate-added X-ray image data obtained as a result of the vertebral region determination unit 804 determining the correlation between the center coordinates calculated by the vertebra detection unit 802 and corresponding cervical vertebrae bodies.

By executing a determination process with respect to the coordinate-added X-ray image data 1110 in the above-described manner, the coordinate-added X-ray image data 1130 indicating the center coordinates of each of the cervical vertebrae bodies from the second cervical vertebra (C2) vertebral body to the seventh cervical vertebra (C7) vertebral body can be obtained.

(iii) Determination Process for MRI Image Data

Figure 12:
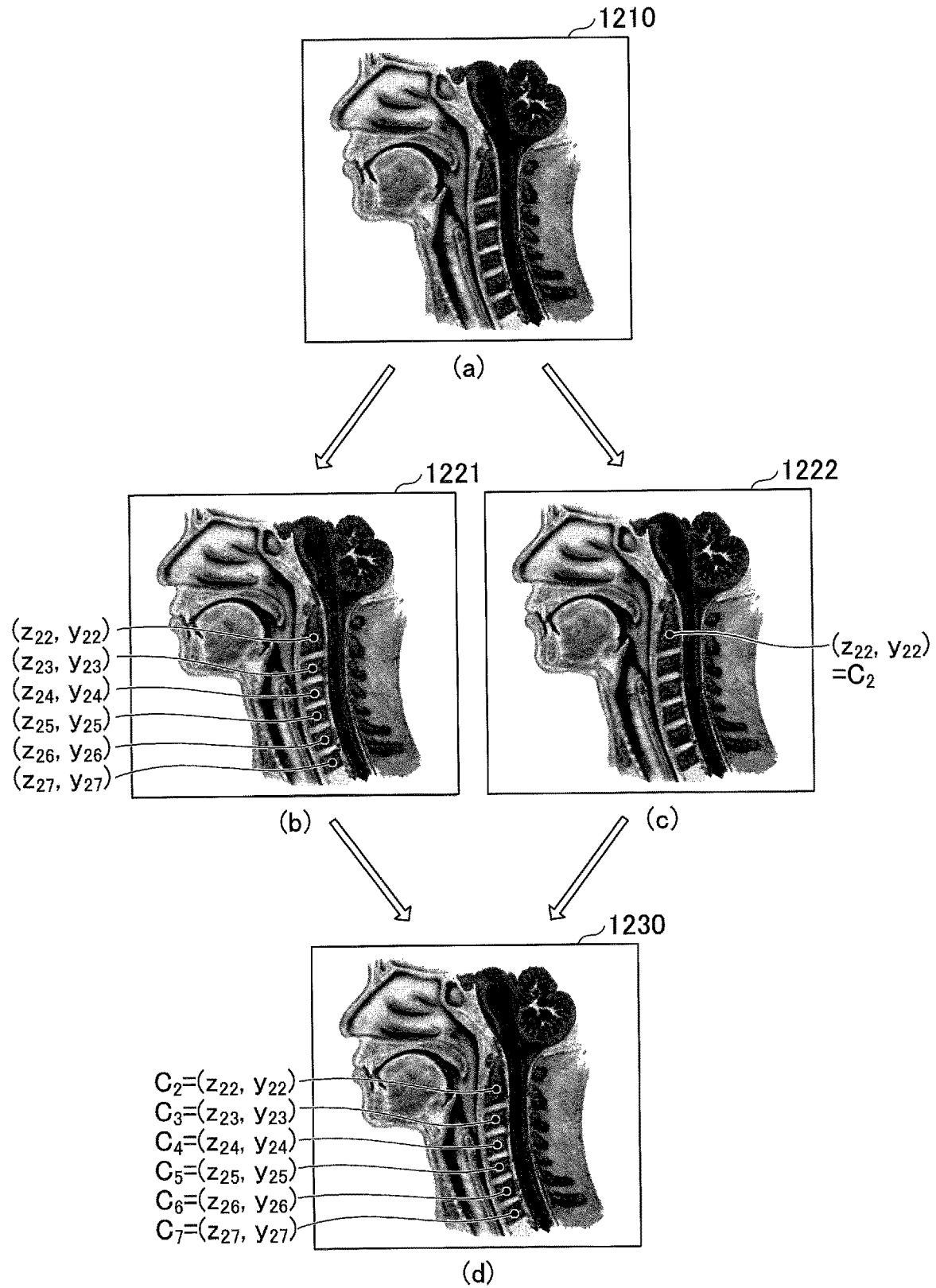
FIG. 12 is a diagram illustrating a first specific example of the determination process executed with respect to MRI image data.

In the following, a specific example of the determination process executed with respect to MRI image data will be described. FIG. 12 is a diagram illustrating a first specific example of the determination process executed with respect to MRI image data. In FIG. 12, MRI image data 1210 represents an example of the MRI image data retrieved by the second medical image data acquisition unit 811.

In FIG. 12, MRI image data 1221 represents an example of MRI image data obtained as a result of the vertebra detection unit 812 performing image processing on the MRI image data 1210 to extract vertebrae or vertebral parts of the subject 300 and calculate the center coordinates of the extracted vertebrae or vertebral parts.

In FIG. 12, MRI image data 1222 represents an example of MRI image data obtained as a result of the specific vertebra detection unit 813 performing image processing on the MRI image data 1210 to extract the second cervical vertebra (C2) vertebral body of the subject 300 and calculate the specific center coordinates of the extracted second cervical vertebra (C2) vertebral body.

In FIG. 12, MRI image data 1230 represents an example of MRI image data obtained as a result of the vertebral region determination unit 814 determining the correlation between the center coordinates calculated by the vertebra detection unit 812 and corresponding cervical vertebrae bodies.

By executing a determination process with respect to the MRI image data 1210 in the above-described manner, the MRI image data 1230 indicating the center coordinates of the each of the cervical vertebrae bodies from the second cervical vertebra (C2) vertebral body to the seventh cervical vertebra (C7) vertebral body can be obtained.

(4) Functional Configuration of Transform Unit included in Registration Data Generation Unit In the following, example detailed functional configurations of the transform unit 820 included in the registration data generation unit 152 will be described. Specifically, four types of transform units having different functional configurations (hereinafter referred to as "first transform unit 1300" to "fourth transform unit 1600") are described below as specific examples of the functional configuration of the transform unit 820 included in the registration data generation unit 152 according to the present embodiment.

(i) Functional Configuration of First Transform Unit

Figure 13A:
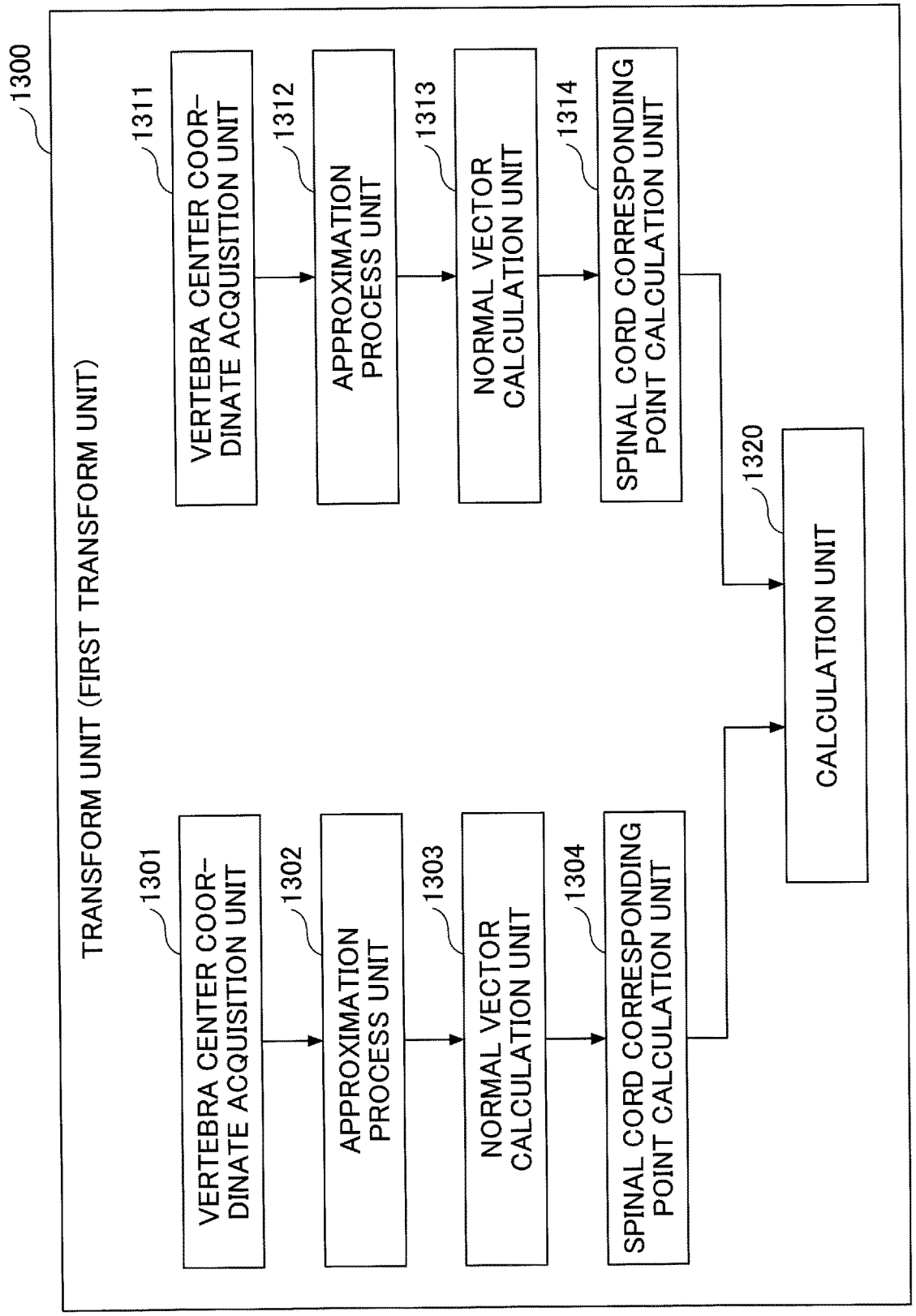
FIGS. 13A and 13B are diagrams illustrating an example functional configuration of a first transform unit.
Figure 13B:
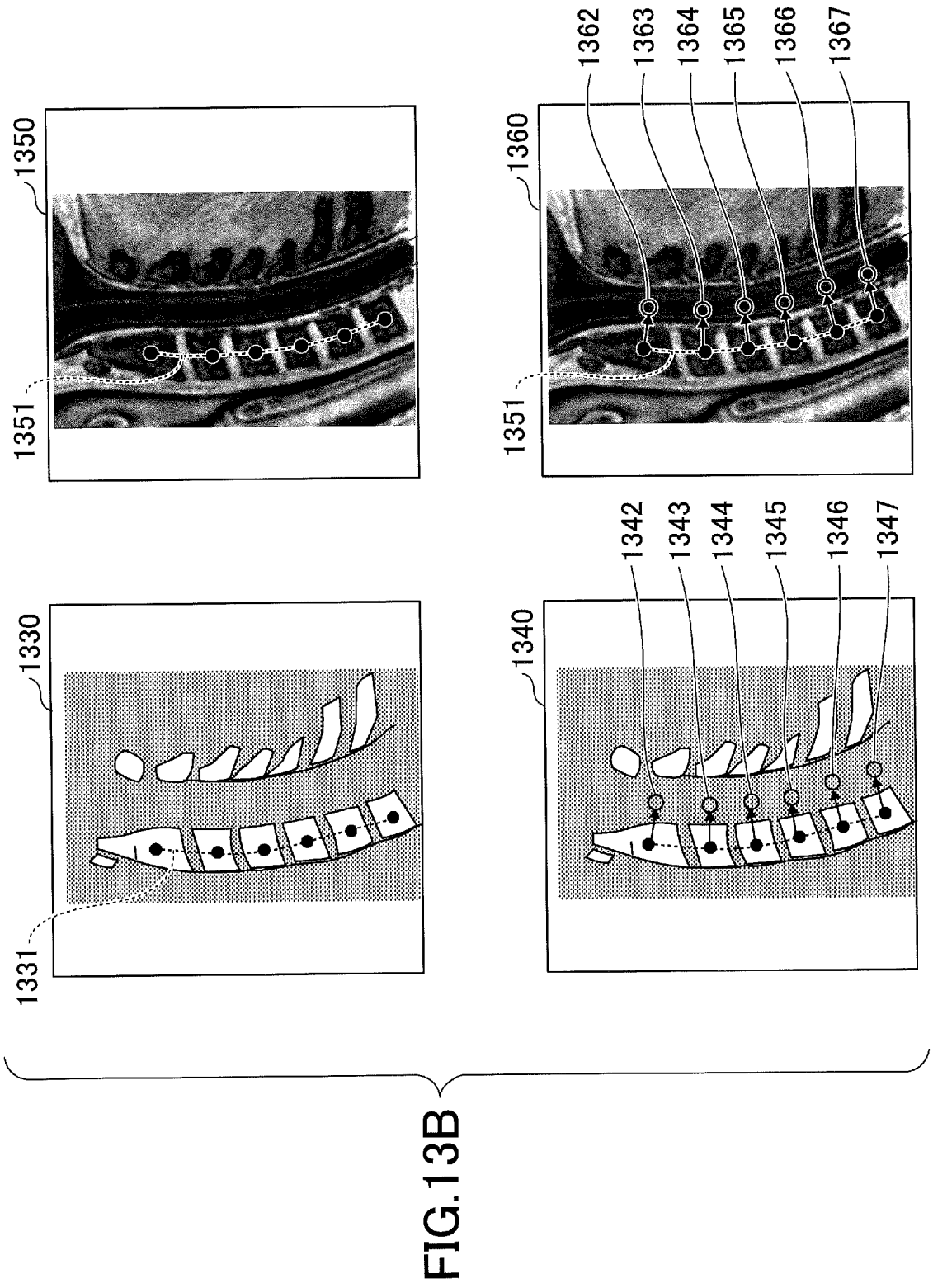

FIGS. 13A and 13B are diagrams illustrating an example functional configuration of the first transform unit 1300. As illustrated in FIG. 13A, the first transform unit 1300 includes a vertebra center coordinate acquisition unit 1301, an approximation process unit 1302, a normal vector calculation unit 1303, and a spinal cord corresponding point calculation unit 1304. The first transform unit 1300 further includes a vertebra center coordinate acquisition unit 1311, an approximation process unit 1312, a normal vector calculation unit 1313, and a spinal cord corresponding point calculation unit 1314. The first transform unit 1300 further includes a calculation unit 1320.

In the following, functions of the above units included in the first transform unit 1300 will be described with reference to FIG. 13B. Note that coordinate-added X-ray image data 1330 in FIG. 13B corresponds to an enlarged view of a part of the coordinate-added X-ray image data 1130 indicating the center coordinates of each of the cervical vertebrae bodies from the second cervical vertebra (C2) vertebral body to the seventh cervical vertebra (C7) vertebral body. Similarly, MRI image data 1350 in FIG. 13B corresponds to an enlarge view of a part of the MRI image data 1230 indicating the center coordinates of each of the cervical vertebrae bodies from the second cervical vertebra (C2) vertebral body to the seventh cervical vertebra (C7) vertebral body.

The vertebra center coordinate acquisition unit 1301 acquires the center coordinates of the second cervical vertebra (C2) vertebral body to the seventh cervical vertebra (C7) vertebral body from the vertebral region determination unit 804 and communicates the acquired center coordinates to the approximation process unit 1302.

The approximation process unit 1302 calculates an approximate curve connecting the center coordinates included in the coordinate-added X-ray image data 1330. In FIG. 13B, a curve 1331 of the coordinate-added X-ray image data 1330 represents an example of the approximate curve calculated by the approximation process unit 1302.

The normal vector calculation unit 1303 calculates a normal vector to the curve 1331 that has a predetermined length and extends from each set of center coordinates toward a corresponding spinous process (toward the right side in the coordinate-added X-ray image data 1330). In FIG. 13B, coordinate-added X-ray image data 1340 indicates arrows that represent the normal vectors calculated by the normal vector calculation unit 1303.

The spinal cord corresponding point calculation unit 1304 is an example of a first calculation unit. The spinal cord corresponding point calculation unit 1304 calculates the coordinates of the tip position of the normal vector calculated by the normal vector calculation unit 1303 as coordinates of a point included in the spinal cord area (spinal cord corresponding point). In FIG. 13B, points 1342 to 1347 in coordinate-added X-ray image data 1340 represent the positions of the spinal cord corresponding points calculated by the spinal cord corresponding point calculation unit 1304.

In this way, the first transform unit 1300 uses the center coordinates of the cervical vertebrae bodies to estimate the coordinates of the spinal cord corresponding points within the coordinate-added X-ray image data 1330 that does not include an image of the spinal cord.

Similarly, the vertebra center coordinate acquisition unit 1311 acquires the center coordinates of the second cervical vertebra (C2) vertebral body to the seventh cervical vertebra (C7) vertebral body from the vertebral region determination unit 814 and communicates the acquired center coordinates to the approximation process unit 1312.

The approximation process unit 1312 calculates an approximate curve connecting the center coordinates included in the MRI image data 1350. In FIG. 13B, a curve 1351 of the MRI image data 1350 represents an example of the approximate curve calculated by the approximation process unit 1312.

The normal vector calculation unit 1313 calculates a normal vector to the curve 1351 that has a predetermined length and extends from each set of center coordinates toward a corresponding spinous process (toward the right side in the MRI image data 1350). In FIG. 13B, MRI image data 1360 indicates arrows representing the normal vectors calculated by the normal vector calculation unit 1313.

The spinal cord corresponding point calculation unit 1314 is an example of a second calculation unit. The spinal cord corresponding point calculation unit 1314 calculates the coordinates of the tip position of the normal vector calculated by the normal vector calculation unit 1313 as coordinates of a point included in the spinal cord area (spinal cord corresponding point). In FIG. 13B, points 1362 to 1367 of the MRI image data 1360 represent the positions of the spinal cord corresponding points calculated by the spinal cord corresponding point calculation unit 1314.

In this way, the first transform unit 1300 uses the center coordinates of cervical vertebrae bodies to estimate the coordinates of the spinal cord corresponding points within the MRI image data 1350.

The calculation unit 1320 is an example of a generation unit. The calculation unit 1320 generates registration data for superimposing the spinal cord corresponding points (points 1342 to 1347) calculated by the spinal cord corresponding point calculation unit 1304 on the spinal cord corresponding points (points 1362 to 1367) calculated by the spinal cord corresponding point calculation unit 1314.

Specifically, the calculation unit 1320 transforms the coordinates of each pixel of the coordinate-added X-ray image data 1340 so that the points 1342 to 1347 may be superimposed on the points 1362 to 1367 of the MRI image data 1360 and communicates the transform data used to perform the coordinate transformation as registration data to the registration data storage control unit 821.

(ii) Functional Configuration of Second Transform Unit

Figure 14A:
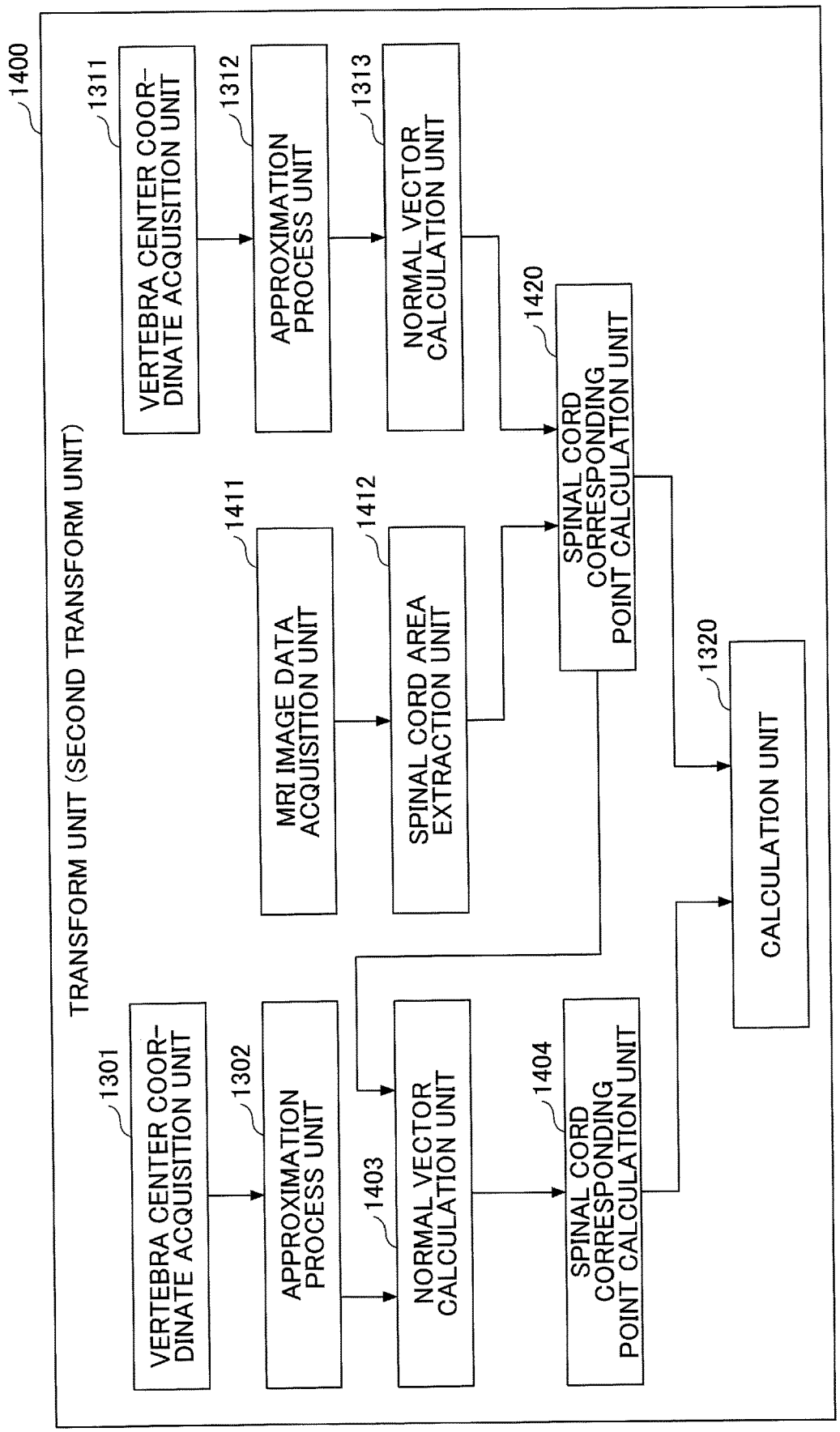
FIGS. 14A and 14B are diagrams illustrating an example functional configuration of a second transform unit.
Figure 14B:
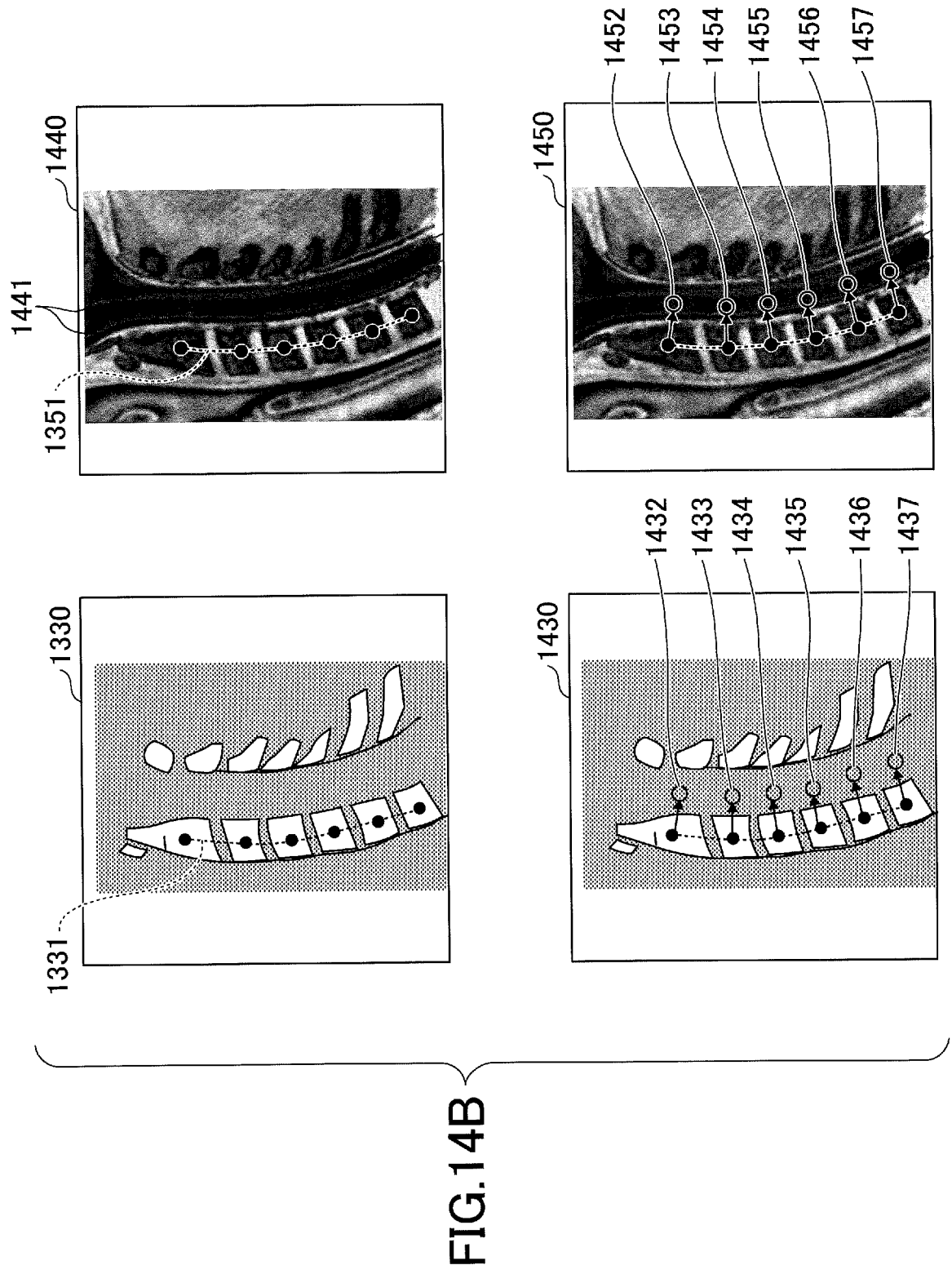

FIGS. 14A and 14B are diagrams illustrating an example functional configuration of the second transform unit 1400. As illustrated in FIG. 14A, the second transform unit 1400 includes a vertebra center coordinate acquisition unit 1301, an approximation process unit 1302, a normal vector calculation unit 1403, and a spinal cord corresponding point calculation unit 1404. The second transform unit 1400 further includes a vertebra center coordinate acquisition unit 1311, an approximation process unit 1312, a normal vector calculation unit 1313, an MRI image data acquisition unit 1411, a spinal cord area extraction unit 1412, a spinal cord corresponding point calculation unit 1420, and a calculation unit 1320.

In the following, functions of the above units included in the second transform unit 1400 will be described with reference to FIG. 14B. Note that functions of the second transform unit 1400 that are substantially identical to those of the first transform unit 1300 are given the same reference numerals and descriptions thereof will be omitted. The following descriptions are primarily focused on functions of the second transform unit 1400 that differ from those of the first transform unit 1300.

The MRI image data acquisition unit 1411 acquires the MRI image data retrieved by the second medical image data acquisition unit 811. In FIG. 14B, MRI image data 1440 represents an example of the MRI image data acquired by the MRI image data acquisition unit 1411. Note that the center coordinates of cervical vertebrae bodies and the curve 1351 are indicated in the MRI image data 1440 of FIG. 14B for the sake of facilitating comprehension.

The spinal cord area extraction unit 1412 extracts a spinal cord area from the MRI image data 1440 acquired by the MRI image data acquisition unit 1411. In FIG. 14B, the MRI image data 1440 includes curves 1441 representing the edges of the spinal cord area.

The spinal cord corresponding point calculation unit 1420 adjusts the length of each normal vector calculated by the normal vector calculation unit 1313 such that the tip position of each normal vector is included within the spinal cord area delimited by the curves 1441. In FIG. 14B, MRI image data 1450 represents an example of MRI image data obtained after the length of each normal vector calculated by the normal vector calculation unit 1313 has been adjusted so that the tip position of each normal vector is included within the spinal cord area delimited by the curves 1441.

By adjusting the length of each normal vector as in the MRI image data 1450 of FIG. 14B, points 1452 to 1457 indicating the tip positions of the normal vectors will all be included within the spinal cord area. The spinal cord corresponding point calculation unit 1420 calculates the coordinates of the points 1452 to 1457 as the coordinates of spinal cord corresponding points.

In this way, the second transform unit 1400 can calculate the coordinates of the spinal cord corresponding points that are included within the spinal cord area based on the center coordinates in the MRI image data 1440.

Also, the spinal cord corresponding point calculation unit 1420 communicates to the normal vector calculation unit 1403, the length of each normal vector (distance between the vertebral body center coordinates and the spinal cord corresponding point) that have been adjusted in calculating the coordinates of the points 1452 to 1457 in the MRI image data 1450.

The normal vector calculation unit 1403 calculates a normal vector to the curve 1331 that extends from each set of center coordinates toward a corresponding spinous process (toward the right side in the coordinate-added X-ray image data 1330). Note that the normal vector calculation unit 1403 uses the length of each normal vector communicated from the spinal cord corresponding point calculation unit 1420 to calculate each normal vector. In FIG. 14B, coordinate-added X-ray image data 1430 indicates arrows representing the normal vectors calculated by the normal vector calculation unit 1403.

The spinal cord corresponding point calculation unit 1404 calculates the coordinates of the tip positions of the normal vectors calculated by the normal vector calculation unit 1403 as coordinates of points included in the spinal cord area (spinal cord corresponding points). In FIG. 14B, points 1432 to 1437 of the coordinate-added X-ray image data 1430 represent the positions of the spinal cord corresponding points calculated by the spinal cord corresponding point calculation unit 1404.

In this way, the second transform unit 1400 estimates the coordinates of the spinal cord corresponding points based on the center coordinates of the coordinate-added X-ray image data 1330 that does not include an image of the spinal cord. Note that the second transform unit 1400 estimates the coordinates of the spinal cord corresponding points based on the distances from the center coordinates to the spinal cord area that are calculated using the MRI image data 1450. As such, the coordinates of the spinal cord corresponding points may be more accurately calculated as compared with the coordinates of the spinal cord corresponding points estimated by the first transform unit 1300.

(iii) Functional Configuration of Third Transform Unit

Figure 15A:
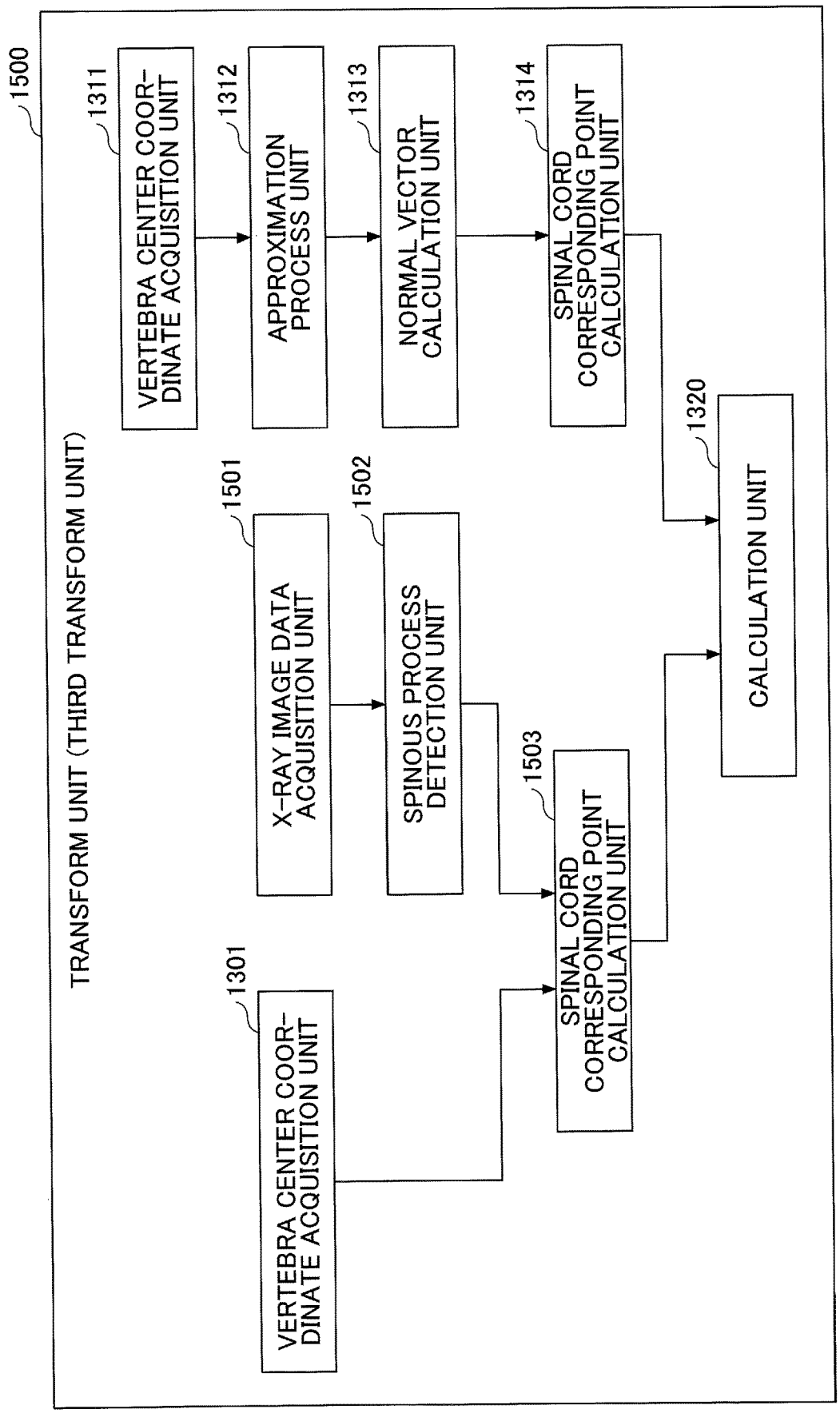
FIGS. 15A and 15B are diagrams illustrating an example functional configuration of a third transform unit.
Figure 15B:
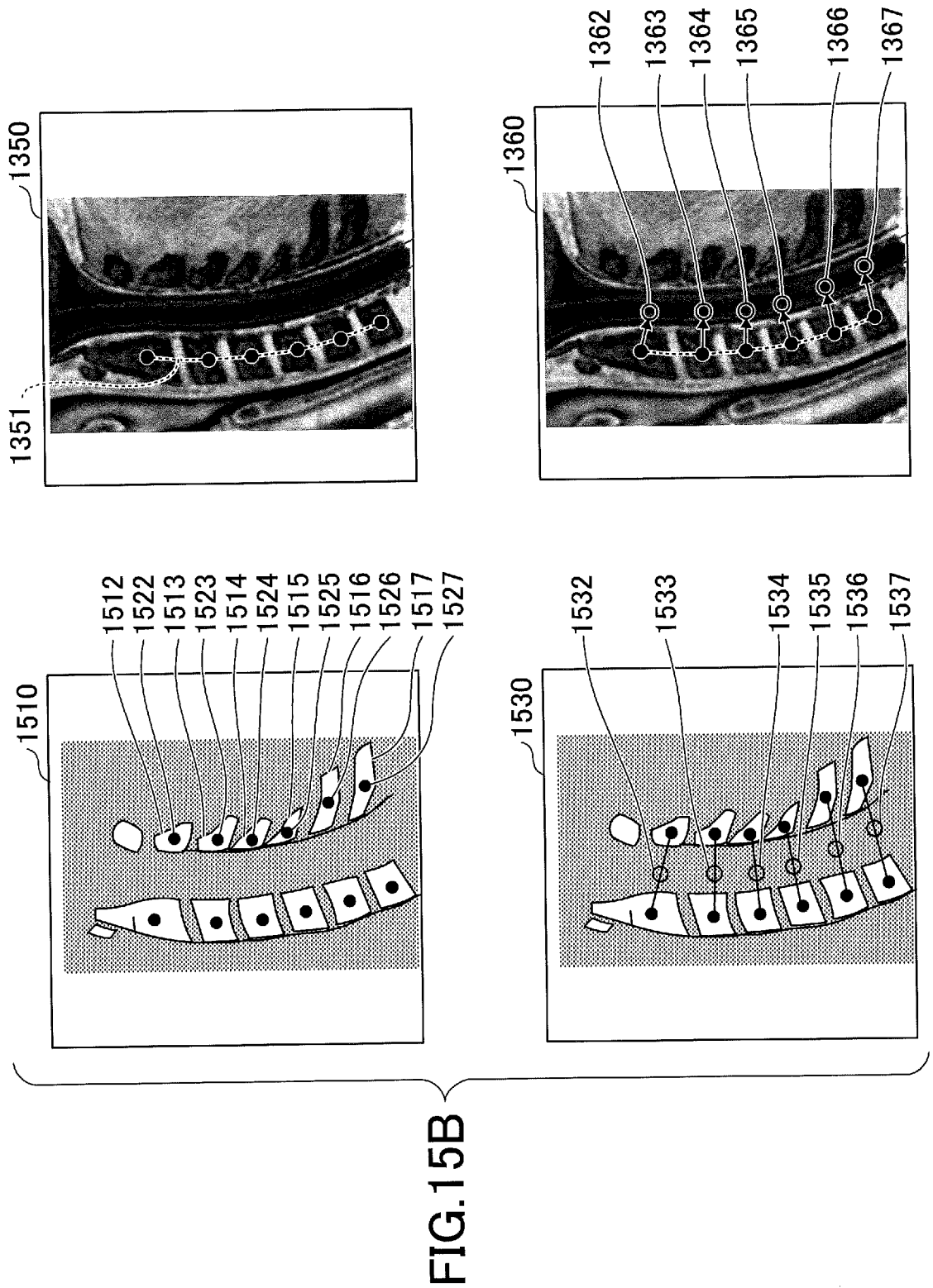

FIGS. 15A and 15B are diagrams illustrating an example functional configuration of the third transform unit 1500. As illustrated in FIG. 15A, the third transform unit 1500 includes a vertebra center coordinate acquisition unit 1301, an X-ray image data acquisition unit 1501, a spinous process detection unit 1502, and a spinal cord corresponding point calculation unit 1503. The third transform unit 1500 further includes a vertebra center coordinate acquisition unit 1311, an approximation process unit 1312, a normal vector calculation unit 1313, a spinal cord corresponding point calculation unit 1314, and a calculation unit 1320.

In the following, functions of the above units of the third transform unit 1500 will be described with reference to FIG. 15B. Note that functions of the third transform unit 1500 that are substantially identical to those of the first transform unit 1300 are given the same reference numerals and descriptions thereof will be omitted. The following descriptions are primarily focused on functions of the third transform unit 1500 that differ from those of the first transform unit 1300.

The X-ray image data acquisition unit 1501 acquires the coordinate-added X-ray image data retrieved by the first medical image data acquisition unit 801. In FIG. 15B, coordinate-added X-ray image data 1510 represents an example of the coordinate-added X-ray image data acquired by the X-ray image data acquisition unit 1501. Note that center coordinates of the cervical vertebrae bodies are indicated in the coordinate-added X-ray image data 1510 of FIG. 15B for the sake of facilitating comprehension.

The spinous process detection unit 1502 extracts spinous processes from the coordinate-added X-ray image data 1510 acquired by the X-ray image data acquisition unit 1501. In the coordinate-added X-ray image data 1510 of FIG. 15B, bold areas 1512 to 1517 represent spinous processes.

Also, the spinous process detection unit 1502 calculates the coordinates of center points 1522 to 1527 of the extracted spinous processes and communicates the calculated coordinates to the spinal cord corresponding point calculation unit 1503.

The spinal cord corresponding point calculation unit 1503 calculates the coordinates of spinal cord corresponding points based on the center coordinates of the second cervical vertebra (C2) vertebral body to the seventh cervical vertebra (C7) vertebral body part communicated from the vertebra center coordinate acquisition unit 1301 and the coordinates of corresponding center points 1522 to 1527 communicated from the spinous process detection unit 1502.

Specifically, the spinal cord corresponding point calculation unit 1503 calculates the coordinates of the midpoint between the center coordinates of the second cervical vertebra (C2) vertebral body and the coordinates of the center point 1522 of the corresponding spinous process (bold area 1512) as estimated coordinates of a spinal cord corresponding point. In FIG. 15B, point 1532 in coordinate-added X-ray image data 1530 represents the position of the spinal cord corresponding point estimated by the spinal cord corresponding point calculation unit 1503.

Similarly, the spinal cord corresponding point calculation unit 1503 calculates the coordinates of the midpoint between the center coordinates of the third cervical vertebra (C3) vertebral body and the coordinates of the center point 1523 of the corresponding spinous process (bold area 1513) as estimated coordinates of a spinal cord corresponding point. In FIG. 15B, point 1533 of the coordinated X-ray image data 1530 represents the position of the spinal cord corresponding point estimated by the spinal cord corresponding point calculation unit 1503.

The spinal cord corresponding point calculation unit 1503 uses the coordinates of the center points 1534 to 1537 in a similar manner to estimate the coordinates of spinal cord corresponding points.

(iv) Functional Configuration of Fourth Transform Unit

Figure 16A:
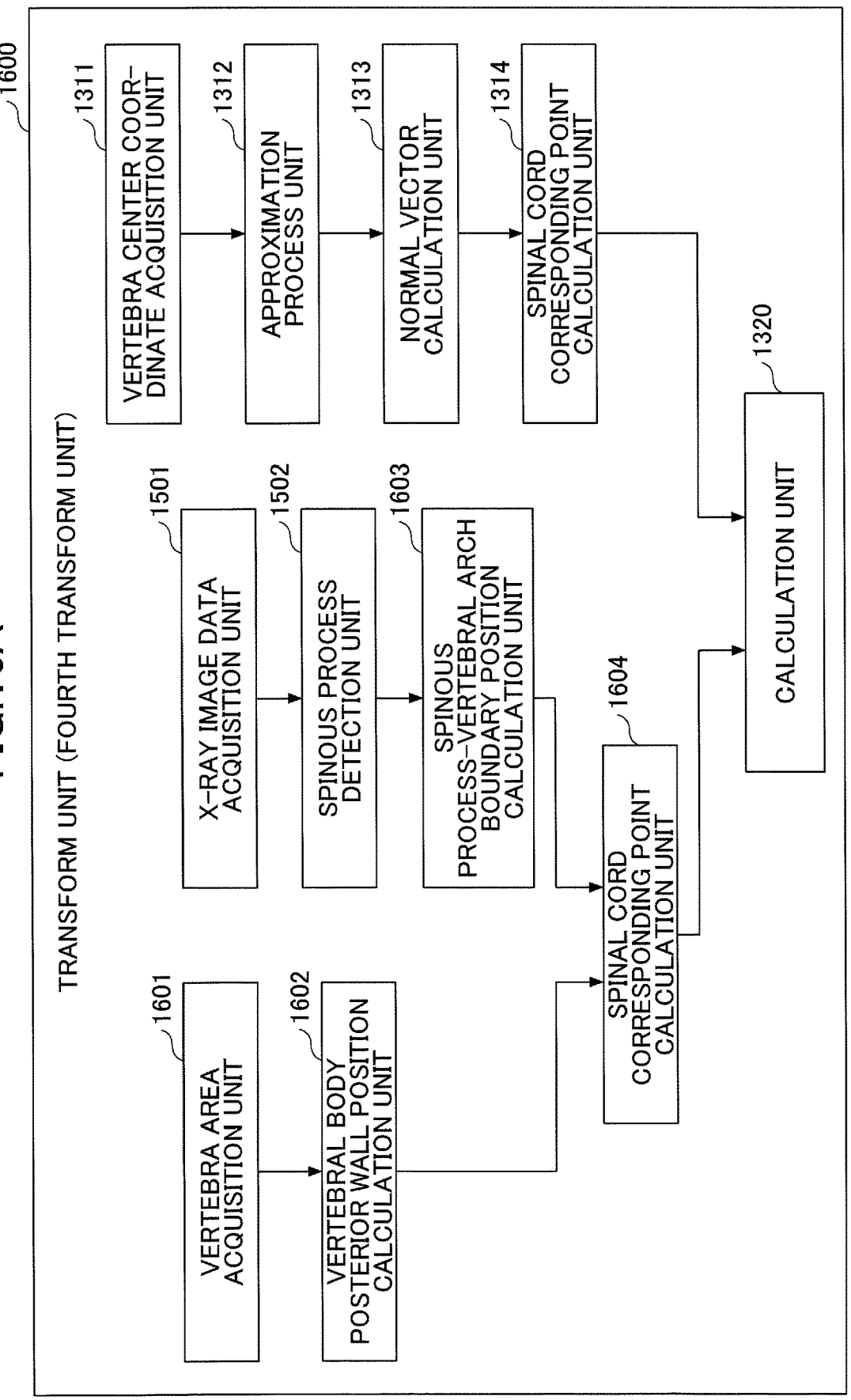
FIGS. 16A and 16B are diagrams illustrating an example functional configuration of a fourth transform unit.
Figure 16B:
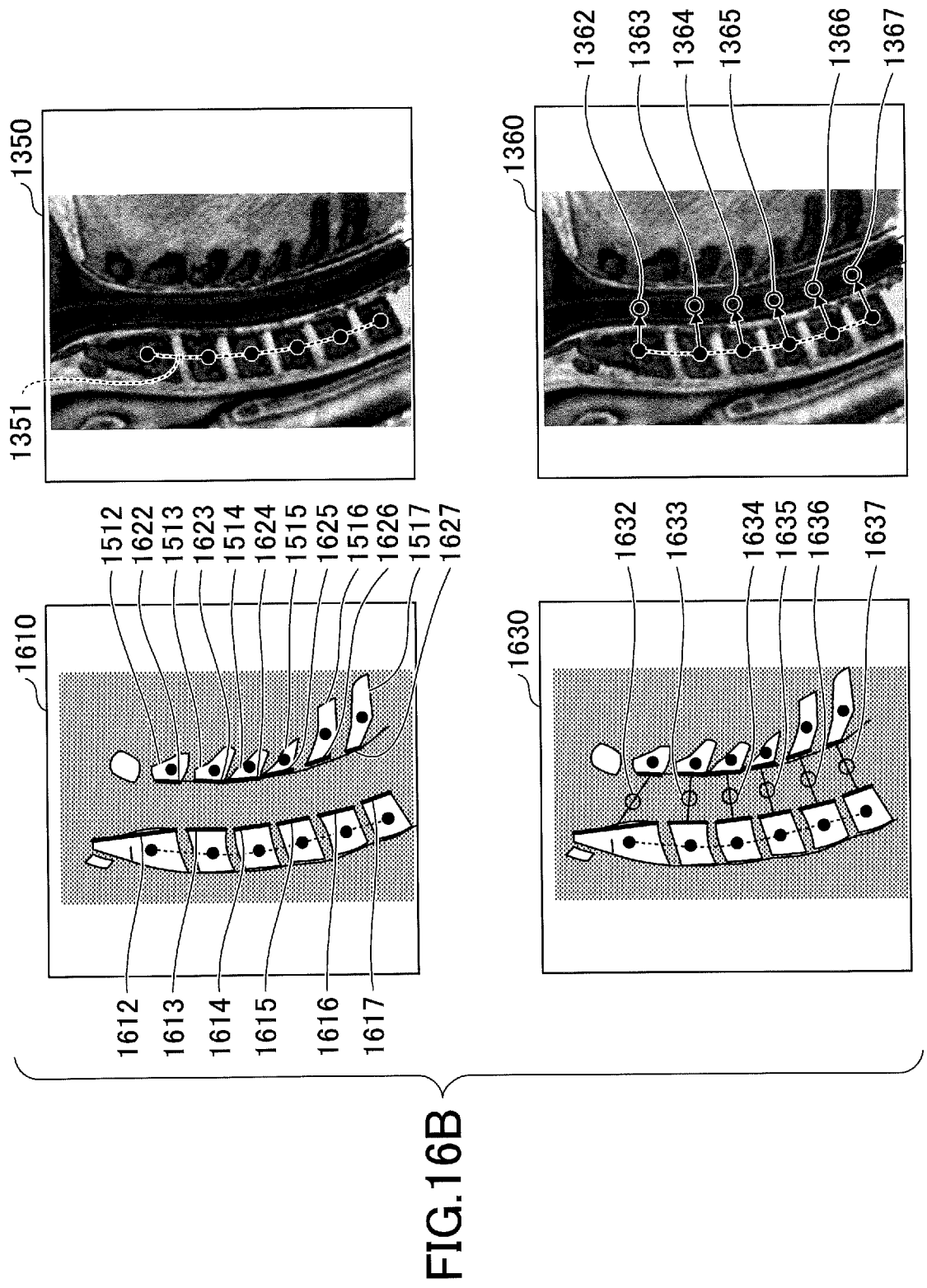

FIGS. 16A and 16B are diagrams illustrating an example functional configuration of the fourth transform unit 1600. As illustrated in FIG. 16A, the fourth transform unit 1600 includes a vertebra area acquisition unit 1601, a vertebral body posterior wall position calculation unit 1602, an x-ray image data acquisition unit 1501, a spinous process detection unit 1502, a spinous process-vertebral arch boundary position calculation unit 1603, and a spinal cord corresponding point calculation unit 1604. The fourth transform unit 1600 further includes a vertebra center coordinate acquisition unit 1311, an approximation process unit 1312, a normal vector calculation unit 1313, a spinal cord corresponding point calculation unit 1314, and a calculation unit 1320.

In the following, functions of the above units of the fourth transform unit 1600 will be described with reference to FIG. 16B. Note that functions of the fourth transform unit 1600 that are substantially identical to those of the third transform unit 1500 are given the same reference numerals and descriptions thereof will be omitted. The following descriptions are primarily focused on functions of the fourth transform unit 1600 that differ from those of the third transform unit 1500.

The vertebra area acquisition unit 1601 acquires the small areas that have been extracted by the vertebra detection unit 802 as vertebra areas corresponding to the second cervical vertebra (C2) vertebral body to the seventh cervical vertebra (C7) vertebral body.

The vertebral body posterior wall position calculation unit 1602 calculates the positions of vertebral body posterior walls based on the small areas corresponding to the second cervical vertebra (C2) vertebral body to the seventh cervical vertebra (C7) vertebral body acquired by the vertebra area acquisition unit 1601. In FIG. 16B, coordinate-added X-ray image data 1610 indicates line segments 1612 to 1617 respectively representing the positions of the vertebral body posterior walls of the second cervical vertebra (C2) to the seventh cervical vertebra (C7).

The spinous process-vertebral arch boundary position calculation unit 1603 calculates the boundary positions between spinous processes and vertebral arches based on the spinous processes detected by the spinous process detection unit 1502. In the coordinate-added X-ray image data 1610 of FIG. 16B, bold areas 1512 to 1517 represent the spinous processes, and line segments 1622 to 1627 represent the boundary positions between the spinous processes and the vertebral arches.

The spinal cord corresponding point calculation unit 1604 calculates the coordinates of spinal cord corresponding points based on the positions of the vertebral body posterior walls of the second cervical vertebra (C2) to the seventh cervical vertebra (C7) communicated from the vertebral body posterior wall position calculation unit 1602 and the boundary positions communicated from the spinous process-vertebral arch boundary position calculation unit 1603.

Specifically, to calculate the coordinates of an estimated position of a spinal cord corresponding point, the spinal cord corresponding point calculation unit 1604 calculates the coordinates of the midpoint between the line segment 1612 representing the ventral body posterior wall of the second cervical vertebra (C2) and the line segment 1622 representing the boundary position between the corresponding spinous process (bold area 1512) and vertebral arch. In FIG. 16B, point 1632 in coordinate-added X-ray image data 1630 represents the position of a spinal cord corresponding point estimated by the spinal cord corresponding point calculation unit 1604 based on the line segment 1612 and the line segment 1622.

Similarly, the spinal cord corresponding point calculation unit 1604 estimates the coordinates of a spinal cord corresponding point by calculating the coordinates of a midpoint between line segment 1613 representing the position of the vertebral body posterior wall of the third cervical vertebra (C3) and line segment 1623 representing the boundary position between the corresponding spinous process (bold area 1513) and vertebral arch. In FIG. 16B, point 1633 of the coordinate-added X-ray image data 1630 represents the position of the spinal cord corresponding point estimated by the spinal cord corresponding point calculation unit 1604 based on the line segment 1613 and the line segment 1623.

Further, the spinal cord corresponding point calculation unit 1604 calculates the coordinates of points 1634 to 1637 based on line segments 1614 to 1617 and line segments 1624 to 1627 in a similar manner to estimate the coordinates of spinal cord corresponding points.

<7.3 Diagnostic Support Apparatus Function (Display Control Unit)>

Figure 17:
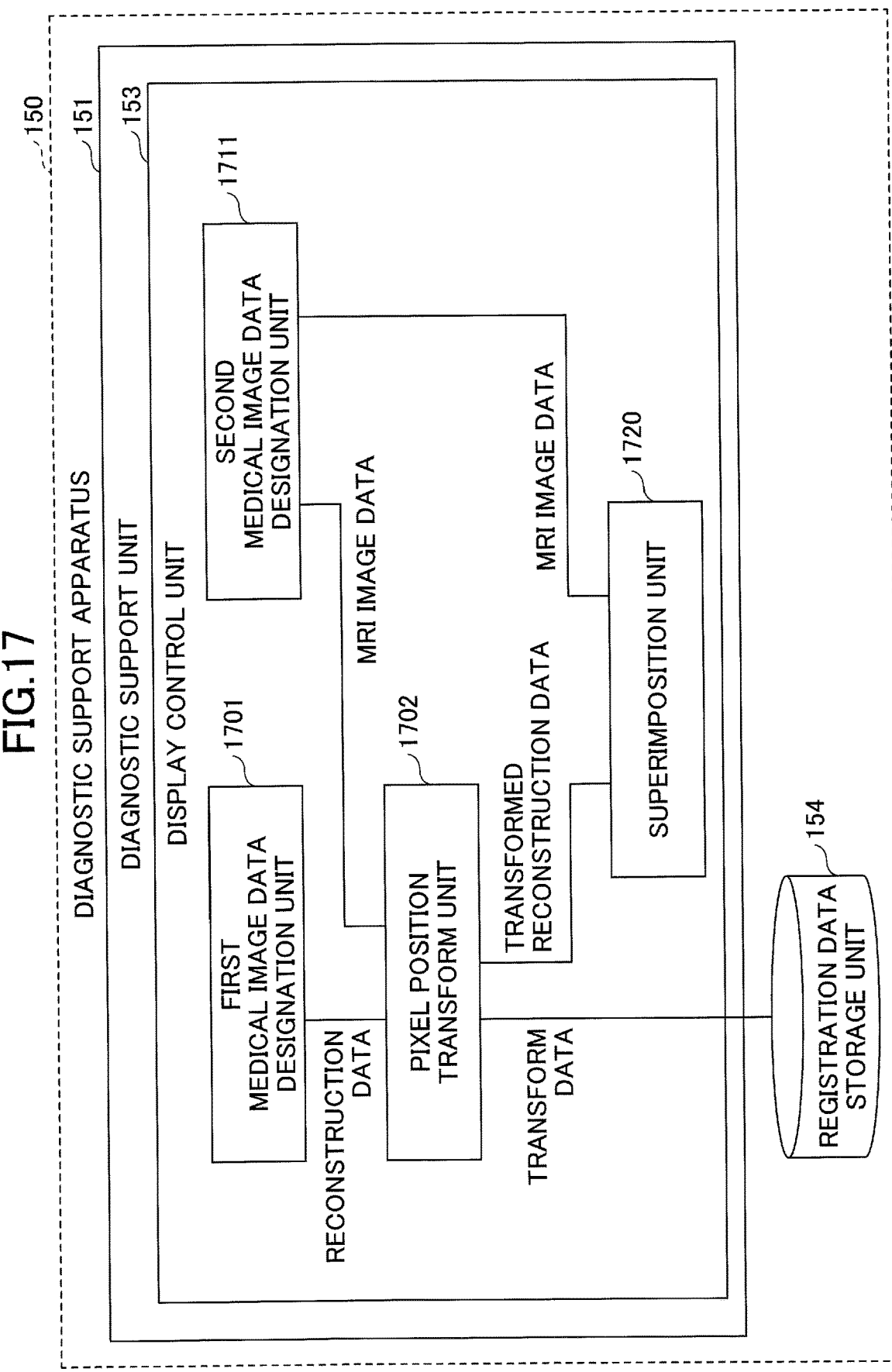
FIG. 17 is a diagram illustrating an example functional configuration of a display control unit.

In the following, the functional configuration of the display control unit 153 included in the diagnostic support unit 151 of the diagnostic support apparatus 150 will be described. FIG. 17 is a diagram illustrating an example functional configuration of the display control unit 153.

In FIG. 17, the display control unit 153 includes a first medical image data designation unit 1701, a pixel position transform unit 1702, a second medical image data designation unit 1711, and a superimposition unit 1720.

The first medical image data designation unit 1701 accepts a designation of reconstruction data from a doctor, for example. Also, the first medical image data designation unit 1701 retrieves the designated reconstruction data from the measurement data storage unit 142 and communicates the retrieved reconstruction data to the pixel position transform unit 1702.

As described above with reference to FIG. 4, for example, the reconstruction data at time $t_1$ may include frames on xy planes at different positions in the z-axis direction. As such, the first medical image data designation unit 1701 extracts from each frame, a pixel at coordinates corresponding to coordinates (z, y) of each pixel of the coordinate-added X-ray image data, and determines the current value of the extracted pixels. In this way, the first medical image data designation unit 1701 can communicate to the pixel position transform unit 1702, reconstruction data frames including the current values of the pixels at the coordinates corresponding to the coordinates of the pixels of the coordinate-added X-ray image data. Note that when extracting pixels from each frame of reconstruction data, it is assumed that the x coordinate value is fixed to a predetermined value.

The first medical image data designation unit 1701 performs similar processes with respect to reconstruction data at times $t_2, t_3, \ldots, t_n$. In this way, the first medical image data designation unit 1701 can communicate to the pixel position transform unit 1702, reconstruction data including a plurality of frames that include the current values of the pixels of the coordinate-added X-ray image data.

The second medical image data designation unit 1711 accepts a designation of MRI image data from a doctor, for example. Also, the second medical image data designation unit 1711 retrieves the designated MRI image data from the measurement data storage unit 142 and communicates the retrieved MRI image data to the pixel position transform unit 1702 and the superimposition unit 1720.

Upon receiving the reconstruction data including a plurality of frames from the first medical image data designation unit 1701, the pixel position transform unit 1702 refers to the registration data storage unit 154. Then, the pixel position transform unit 1702 retrieves the transform data associated with the combination of the coordinate-added X-ray image data and the MRI image data communicated from the second medical image data designation unit 1711.

Further, the pixel position transform unit 1702 uses the retrieved transform data to transform the coordinates of the pixels of each of the plurality of frames included in the reconstruction data communicated from the first medical image data designation unit 1701 and generate transformed reconstruction data. The pixel position transform unit 1702 communicates the transformed reconstruction data to the superimposition unit 1720.

Note that the pixel position transform unit 1702 is able to transform the coordinates of the pixels in each frame included in the reconstruction data using the retrieved transform data because the coordinates of the pixels in each frame included in the reconstruction data correspond to the coordinates of the pixels of the coordinate-added X-ray image data. That is, the positions in each frame of the reconstruction data associated with coordinates of a diagnosis target organ (spinal cord) included in the coordinate-added X-ray image data correspond to positions of the diagnosis target organ (spinal cord).

As a result, by transforming the coordinates of the pixels in each frame included in the reconstruction data using the retrieved transform data, the current value data of the current flowing in the diagnosis target organ (spinal cord) can be superimposed on the diagnosis target organ (spinal cord) in the MRI image data.

The superimposition unit 1720 superimposes the transformed reconstruction data communicated from the pixel position transform unit 1702 on the MRI image data communicated from the second medical image data designation unit 1711. In this way, the superimposition unit 1720 can display superimposed image data obtained as a result of superimposing corresponding current values of the transformed reconstruction data (grayscale image data representing the current values) on positions of the spinal cord in the MRI image data.

<8. Summary>

As can be appreciated from the above description, the diagnostic support system according to the present embodiment is configured to implement processes of:

- associating the pixels of X-ray image data with the pixels of reconstruction data;
- estimating or extracting the position of the spinal cord from each of the X-ray image data and the MRI image data, and calculating transform data for superimposing the estimated or extracted positions of the spinal cord, and
- transforming the reconstruction data using the calculated transform data, superimposing the transformed reconstruction data on the MRI image data, and displaying the resulting superimposed image data.

According to an aspect of the present embodiment, a plurality of medical images (reconstruction data and MRI image data) obtained with respect to a diagnosis target organ (spinal cord) can be superimposed and displayed.

Second Embodiment

In the first embodiment, the first to fourth transform units 1300 to 1600 are described as specific examples of the transform unit 820, and the diagnostic support apparatus 150 is configured to implement the functions of one of the above transform units. However, according to a second embodiment, the diagnostic support apparatus 150 may include each of the first to fourth transform units 1300 to 1600, and the diagnostic support apparatus 150 may be configured to select one of the transform units automatically or based on an instruction from a doctor, for example. The following descriptions are primarily focused on features of the second embodiment that differ from those of the first embodiment.

Figure 18:
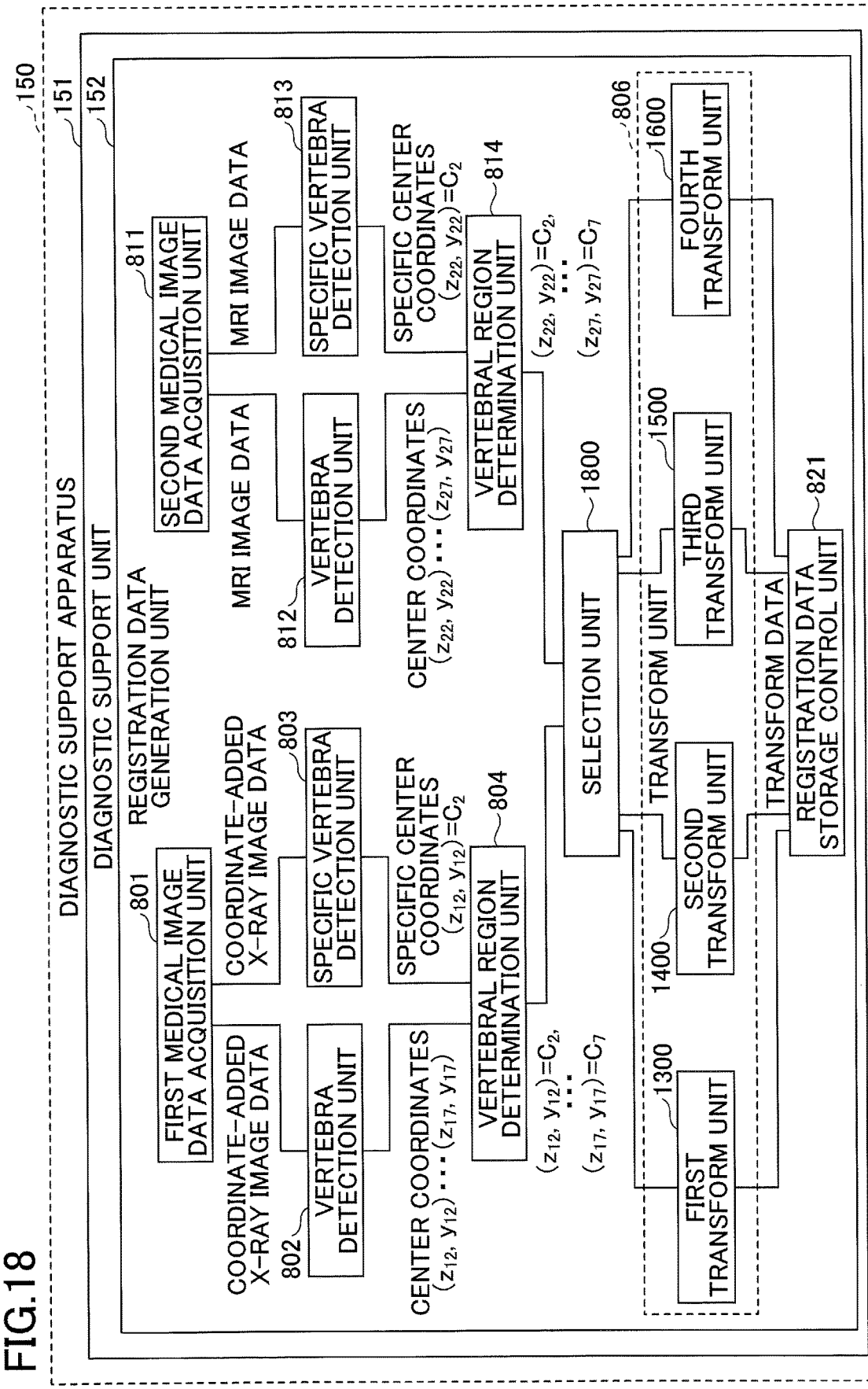
FIG. 18 is a diagram illustrating a second example functional configuration of the registration data generation unit.

FIG. 18 is a diagram illustrating an example functional configuration of the registration data generation unit 152 included in the diagnostic support unit 151 of the diagnostic support apparatus 150 according to the second embodiment. The functional configuration of FIG. 18 differs from that illustrated in FIG. 8 in that the registration data generation unit 152 further includes a selection unit 1800 and a transform unit 806 including the first transform unit 1300 to the fourth transform unit 1600.

The selection unit 1800 selects one transform unit from among the first transform unit 1300 to the fourth transform unit 1600 included in the transform unit 806. The first to fourth transform units 1300 to 1600 have the following characteristics.

The first transform unit 1300 estimates the position of the spinal cord based on center coordinates of a vertebra or a vertebral part, and as such, the spinal cord does not have to be directly extracted from medical image data. Thus, the first medical image data and the second medical image data may be any type of medical image data from which a vertebra or a vertebral part can be extracted.

The second transform Unit 1400 directly extracts the position of the spinal cord from medical image data, and as such, at least one of the first medical image data and the second medical image data has to be medical image data captured by the MRI imaging unit 130.

The third transform unit 1500 estimates the position of the spinal cord based on the center coordinates of a vertebra and the center coordinates of a spinous process, and as such, the spinal cord does not have to be directly extracted from medical image data. However, a vertebra and a spinous process have to be extractable from the medical image data.

The fourth transform unit 1600 estimates the position of the spinal cord based on the position of a vertebral body posterior wall and the boundary position between a spinous process and a vertebral arch, as such the spinal cord does not have to be directly extracted from medical image data. However, a vertebra, a spinous process, and a vertebra arch have to be extractable from the medical image data.

In view of the above characteristics of the transform units and the extraction circumstance of extracting organs/regions from the first medical image data acquired by the first medical image data acquisition unit 801 and the second medical image data acquired by the second medical image data acquisition unit 811, the selection unit 1800 selects one of the transform units to be implemented.

According to an aspect of the diagnostic support system of the present embodiment, an optimum transform unit can be selected from a plurality of transform units such that registration accuracy of medical image data may be improved.

Third Embodiment

In the first and second embodiments described above, it is assumed that a determination process is executed with respect to medical image data of a region including the second cervical vertebra (C2) to the seventh cervical vertebra (C7) as predetermined organs. Thus, in the above embodiments, the specific vertebra detection units 803 and 813 extract the second cervical vertebra (C2) vertebral body as a referential organ (vertebra) to be used as a reference. However, a region captured in medical image data is not limited to the above. For example, when a determination process is executed with respect to medical image data of a region including lumbar vertebrae as predetermined organs, the specific vertebra detection units 803 and 813 may extract the sacrum as a referential organ (vertebra) to be used as a reference.

(i) Determination Process for Coordinate-Added X-Ray Image Data

Figure 19:
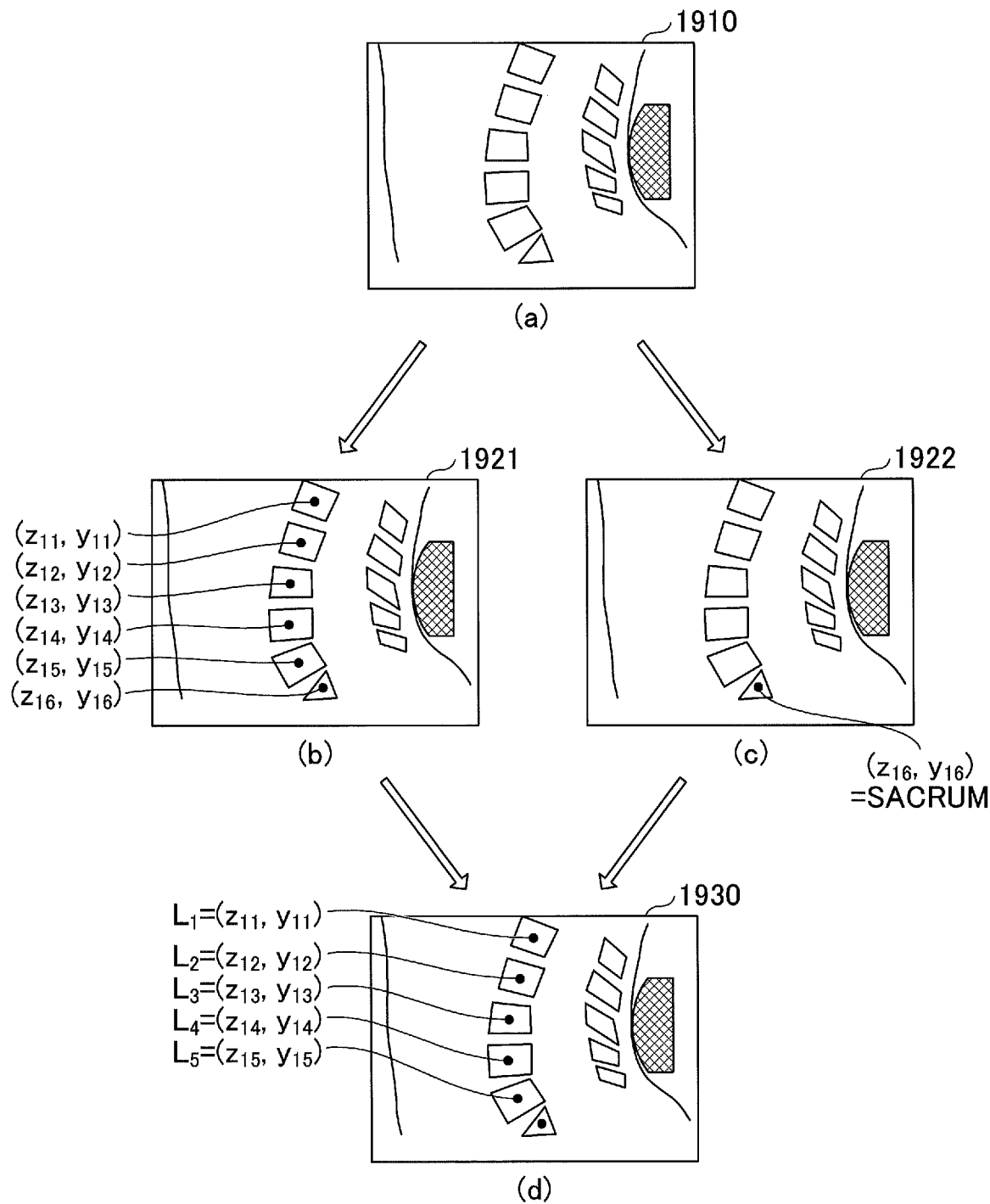
FIG. 19 is a diagram illustrating a second specific example of the determination process executed with respect to coordinate-added X-ray image data.

FIG. 19 is a diagram illustrating a second specific example of the determination process executed with respect to coordinate-added X-ray image data. In FIG. 19, coordinate-added x-ray image data 1910 represents an example of coordinate-added x-ray image data of a region including the lumbar vertebrae of the subject 300 that has been retrieved by the first image data acquisition unit 801.

In FIG. 19, coordinate-added x-ray image data 1921 represents an example of coordinate-added x-ray image data obtained as a result of the vertebra detection unit 802 performing image processing on the coordinate-added X-ray image data 1910 to extract the vertebral bodies of the lumbar vertebrae of the subject 300 and calculate center coordinates of the extracted lumbar vertebrae vertebral bodies.

In FIG. 19, coordinate-added X-ray image data 1922 represents an example of coordinate-added X-ray image data obtained as a result of the specific vertebra detection unit 803 performing image processing on the coordinate-added X-ray image data 1910 to extract the sacrum of the subject 300 and calculate specific center coordinates of the extracted sacrum.

In FIG. 19, coordinate-added X-ray image data 1930 represents an example of coordinate-added X-ray image data obtained as a result of the vertebral region determination unit 804 determining the correlation between the calculated center coordinates and corresponding lumbar vertebrae vertebral bodies.

By executing a determination process with respect to the coordinate-added X-ray image data 1910 in the above-described manner, the coordinate-added X-ray image data 1930 indicating the center coordinates of each of the vertebral bodies of the lumbar vertebrae L1 to L5 can be obtained.

(ii) Determination Process for MRI Image Data

Figure 20:
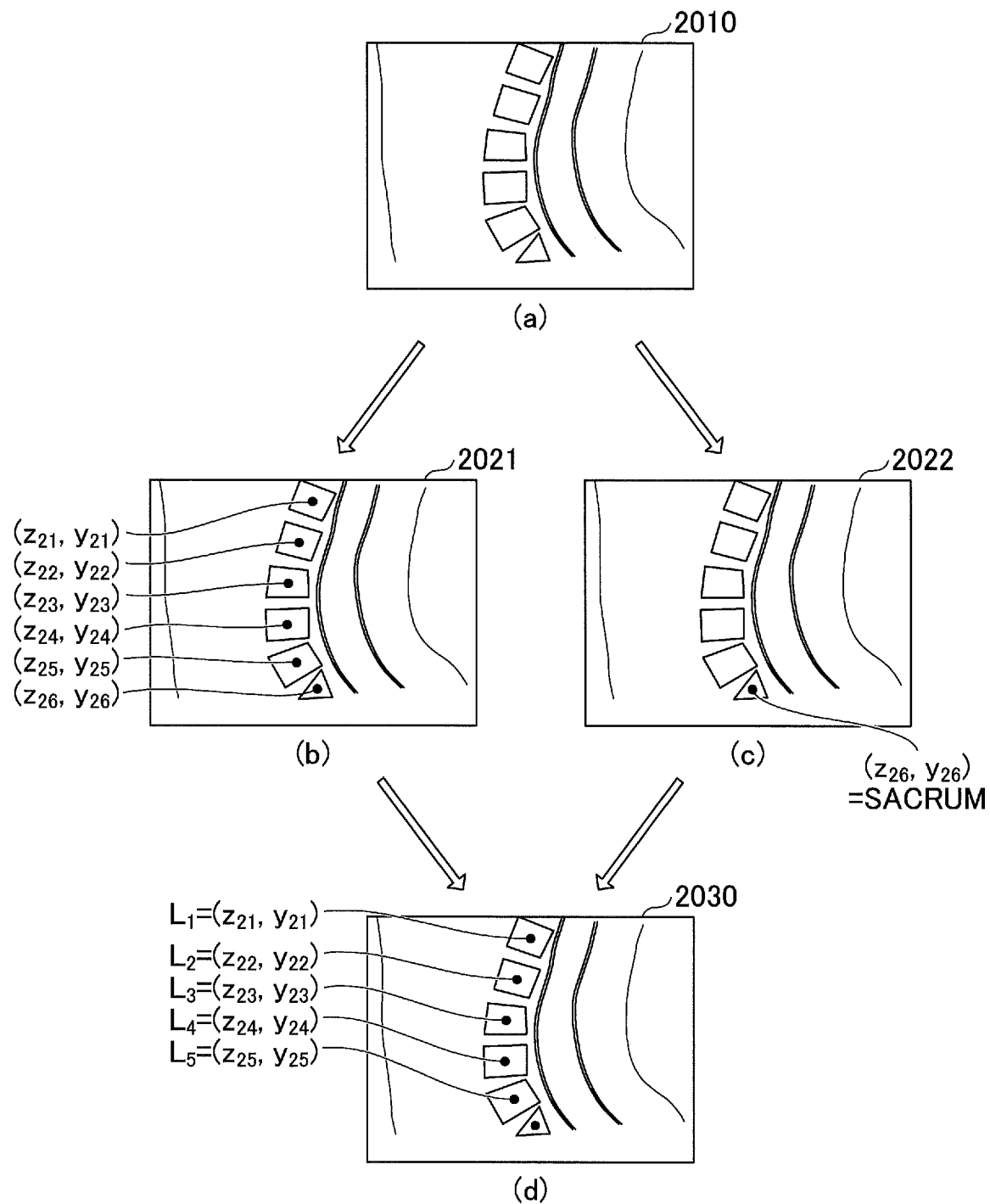
FIG. 20 is a diagram illustrating a second specific example of the determination process executed with respect to MRI image data.

FIG. 20 is a diagram illustrating a second specific example of the determination process executed with respect to MRI image data. In FIG. 20, MRI image data 2010 represents an example of MRI image data of a region including the lumbar vertebrae of the subject that has been retrieved by the second medical image data acquisition unit 811.

In FIG. 20, MRI image data 2021 represents an example of MRI image data obtained as a result of the vertebra detection unit 812 performing image processing on the MRI image data 2010 to extract vertebral bodies of the lumbar vertebrae of the subject 300 and calculate center coordinates of the extracted lumbar vertebrae vertebral bodies.

In FIG. 20, MRI image data 2022 represents an example of MRI image data obtained as a result of the specific vertebra detection unit 813 performing image processing on the MRI image data 2010 to extract the sacrum of the subject 300 and calculate specific center coordinates of the extracted sacrum.

In FIG. 20, MRI image data 2030 represents an example MRI image data obtained as a result of the vertebral region determination unit 814 determining the correlation between the calculated center coordinates and corresponding lumbar vertebrae vertebral bodies.

By executing a determination process with respect to the MRI image data 2010 in the above-described manner, the MRI image data 2030 indicating the center coordinates of each of the vertebral bodies of the lumbar vertebrae L1 to L5 can be obtained.

Other Embodiments

In the above-described embodiments, the second cervical vertebra or the sacrum is extracted by the specific vertebra detection units 803 and 813 as an example of a specific vertebra to be used as a reference. However, the vertebra extracted by the specific vertebra detection units 803 and 813 as the specific vertebra to be used as a reference is not limited to the above. For example, the first cervical vertebra, the sacral vertebra, or the caudal vertebra may be extracted as the specific vertebra. Further, the detection target of the specific vertebra detection units 803 and 813 is not limited to a vertebra and may be a rib or some other detectable organ, for example.

Also, in the above-described embodiments, the transform unit 820 or the transform unit 806 uses a vertebra, a spinous process, a vertebral arch, and the like to estimate a spinal cord corresponding point. However, an organ other than a vertebra, a spinous process, or a vertebral arch (e.g., intervertebral joint) may be used to estimate the spinal cord corresponding point.

Also, in the above-described embodiments, the MRI image data acquisition unit 1411 and the spinal cord area extraction unit 1412 are added to the second transform unit 1400, and spinal cord corresponding points are calculated after extracting the spinal cord area. However, the MRI image data acquisition unit 1411 and the spinal cord area extraction unit 1412 may also be added to a transform unit other than the second transform unit 1400 to enable extraction of the spinal cord area before calculating spinal cord corresponding points.

Also, in the above-described embodiments, X-ray image data of the subject 300 is captured from a lateral side of the subject 300 and the coordinate-added X-ray image data having y-z coordinates mapped to the X-ray image data is generated. However, the imaging direction for capturing the X-ray image data is not limited to the above, and for example, X-ray image data may be captured from the front side of the subject 300 and coordinate-added X-ray image data having x-y coordinates mapped to the X-ray image data may be generated. In this way, superimposed image data having reconstruction data superimposed on MRI image data of an x-y plane may be displayed.

Although the present invention has been described above with reference to certain illustrative embodiments, the present invention is not limited to these embodiments, and numerous variations and modifications may be made without departing from the scope of the present invention.

What is claimed is:

1. A diagnostic support system comprising:
a processor;
a memory; and
a display device,
wherein the memory includes instructions, which when executed, cause the processor to executing the following steps:
generating registration data by defining a coordinate system in first medical image information so that a first reference position in the first medical image information matches the first reference position in data that visualizes magnetic field measurement data, and that a first set of one or more pixels of the first medical image information corresponds to a specific first set of one or more points in the data that visualizes the magnetic field measurement data;
defining correspondence between second medical image information and the registration data so that a second reference position in the second medical image information matches the second reference position in the registration data, and that a second set of one or more points in the second medical image information corresponds to a specific second set of one or more pixels of the registration data;
obtaining superimposed image information by superimposing the data that visualizes the magnetic field measurement data on the second medical image information based on the registration data, so that a position of a target organ in the data that visualizes magnetic field measurement data matches a corresponding position of the target organ in the second medical image information; and
causing the display device to display the superimposed image information.

2. The diagnostic support system according to claim 1, wherein the position of the target organ in the data that visualizes magnetic field measurement data is calculated based on positions of a plurality of organs extracted from the registration data, and the corresponding position of the target organ in the second medical image information is calculated based on positions of a plurality of organs extracted from the second medical image information.

3. A method executed by a diagnostic support system, the method comprising:
generating registration data by defining a coordinate system in first medical image information so that a first reference position in the first medical image information matches the first reference position in data that visualizes magnetic field measurement data, and that a first set of one or more pixels of the first medical image information corresponds to a specific first set of one or more points in the data that visualizes the magnetic field measurement data;

defining correspondence between second medical image information and the registration data so that a second reference position in the second medical image information matches the second reference position in the registration data, and that a second set of one or more points of the second medical image information corresponds to a specific second set of one or more pixels of the registration data;

obtaining superimposed image information by superimposing the data that visualizes the magnetic field measurement data on the second medical image information based on the registration data, so that a position of a target organ in the data that visualizes magnetic field measurement data matches a corresponding position of the target organ in the second medical image information; and displaying the superimposed image information.

* * * * *